United States Patent
Muramatsu et al.

(10) Patent No.: US 6,972,191 B2
(45) Date of Patent: *Dec. 6, 2005

(54) METHOD FOR PRODUCTION OF GERANYLGERANIOL AND ANALOGOUS COMPOUNDS THEREOF BY MICROORGANISMS

(75) Inventors: Masayoshi Muramatsu, Aichi (JP); Shusei Obata, Nagoya (JP); Sakayu Shimizu, Kyoto (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/022,695

(22) Filed: Dec. 20, 2001

(65) Prior Publication Data

US 2002/0187532 A1 Dec. 12, 2002

(30) Foreign Application Priority Data

Dec. 28, 2000 (JP) .......................... 2000/401266
Dec. 10, 2001 (JP) .......................... 2001/376173

(51) Int. Cl.$^7$ ................................. C12P 7/02
(52) U.S. Cl. .............. 435/155; 435/157; 435/171; 435/132; 435/169; 435/170
(58) Field of Search .................. 435/155, 157, 435/171, 132

(56) References Cited

U.S. PATENT DOCUMENTS

| | | | |
|---|---|---|---|
| 5,773,273 A | 6/1998 | Nishino et al. | |
| 6,040,165 A | 3/2000 | Narita et al. | |
| 6,225,096 B1 | 5/2001 | Narita et al. | |
| 6,242,227 B1 * | 6/2001 | Millis et al. | 435/125 |

FOREIGN PATENT DOCUMENTS

| | | |
|---|---|---|
| WO | WO 00/01649 | 1/2000 |
| WO | WO 00/01650 | 1/2000 |
| WO | WO 00/01685 | 1/2000 |
| WO | WO 00/01686 | 1/2000 |

OTHER PUBLICATIONS http://www.atcc.org (ATCC Catalogs).*
C. Chambon et al.: "Isolation and properties of yeast mutants affected in farnesyl diphosphate synthetase", Current Genetics (1990) vol. 18, pp. 41–46.
Hornby et al.: "Quorum Sensing in the Dimorphic Fungus *Candida albicans* Is Mediated by Farnesol", Applied and Environmental Microbiology (2001), vol. 67, No. 7, pp. 2982–2992.
Luis Zea, et al.: *Content of free terpenic compounds in cells and musts during vinification with three Saccharomyces cerevisiae races* Journal of Agricultural and Food Chemistry, vol. 43, No. 4, 1995, pp. 1110–1114.
Rodopulo A. K. et al.: The Effect of Cultivation Conditions on Biosynthesis and Accumulation of Aroma–Bearing Substances, Prikladnaya Biokhimiya I Mikrobiologiya, vol. 21, No. 3, 1985, pp. 412–416.

* cited by examiner

*Primary Examiner*—Irene Marx
(74) *Attorney, Agent, or Firm*—Kenyon & Kenyon

(57) ABSTRACT

The present invention provides a method for producing geranylgeraniol and analogous compounds thereof, which comprises culturing yeast cells (ascomycetes and deuteromycetes), bacterial cells, actinomycete cells or filamentous fungus cells, all of which are capable of producing geranylgeraniol and analogous compounds thereof, in a medium to produce and accumulate geranylgeraniol and analogous compounds thereof in the cells and/or in the extracellular environment; and then collecting these compounds. The present invention enables inexpensive mass production of geranylgeraniol and analogous compounds thereof by using microorganisms capable of producing geranylgeraniol, farnesol and/or nerolidol useful as biosynthetic intermediates of terpenes, carotenoids and/or steroids.

2 Claims, No Drawings

METHOD FOR PRODUCTION OF GERANYLGERANIOL AND ANALOGOUS COMPOUNDS THEREOF BY MICROORGANISMS

FIELD OF THE INVENTION

The present invention relates to a method for production of geranylgeraniol and analogous compounds thereof using microorganisms.

BACKGROUND OF THE INVENTION

Geranylgeraniol and farnesol are believed to be produced in organisms through hydrolysis of geranylgeranyl pyrophosphate and farnesyl pyrophosphate with a phosphatase. Geranylgeranyl pyrophosphate is a pyrophosphate ester of geranylgeraniol, which is yielded by condensation between isopentenyl pyrophosphate and farnesyl pyrophosphate or condensation between three molecules of isopentenyl pyrophosphate and dimethyl aryl pyrophosphate. Geranylgeranyl pyrophosphate is metabolized into a diterpene compound (e.g., gibberellin) by cyclization, into a carotenoid compound via phytoene formed by tail-to-tail condensation, or into polyprenylpyrophosphate by head-to-tail condensation with isopentenyl pyrophosphate. On the other hand, farnesyl pyrophosphate is yielded by condensation between isopentenyl pyrophosphate and geranyl pyrophosphate or condensation between two molecules of isopentenyl pyrophosphate and dimethyl aryl pyrophosphate. Farnesyl pyrophosphate is metabolized into a sesquiterpene compound by cyclization, into steroid and triterpene compounds via squalene formed by tail-to-tail condensation, or into polyprenylpyrophosphate or dolichol by head-to-tail condensation with isopentenyl pyrophosphate. It is also metabolized into a prenylated protein when linked to a cysteine residue of a specific protein such as Ras protein or G protein. Thus, a series of geranylgeraniol derivatives, including geranylgeraniol, geranylgeranyl pyrophosphate and precursors thereof, i.e., farnesyl pyrophosphate, farnesol, geranyl pyrophosphate or geraniol, are dominant compounds as biosynthetic intermediates of terpenes, carotenoids or steroids. In addition, geranylgeraniol and analogous compounds thereof are important for use in the production of perfume, a taxane compound having an anti-tumor activity (Japanese Patent Application No. 8-227481), a hair tonic (Japanese Patent Application No. 8-180449), a therapeutic agent for osteoporosis (Japanese Patent Application No. 9-294089) and the like.

In the production of the geranylgeraniol derivatives stated above, there has been reported a technique for producing geranylgeraniol and/or geranylgeranyl pyrophosphate by culturing plant cells belonging to Euphorbiaceae under light irradiation (Japanese Patent Application Laying-Open (kokai) No. 9-238692), and a technique for allowing an erg mutant of *Saccharomyces cerevisiae* to produce and secrete farnesol [Curr. Genet., 18, 41–46 (1990)], but no naturally occurring cell has been reported to produce geranylgeraniol and/or farnesol. Among these prior techniques, in the technique using plant cells, light irradiation is essential to culture the cells and mass production is difficult because of expensive medium ingredients. Also, in the technique using the erg mutant, it is difficult for this mutant to survive in nature because it cannot synthesize ergosterol essential for yeast growth and it therefore requires the addition of expensive ergosterol to a medium. In contrast, if there is found a wild-type strain producing geranylgeraniol and/or farnesol that can be grown at a higher speed than plant cells and in an inexpensive medium without addition of any specific ingredient, such a strain would enable mass production of intermediates for the above effective substances and therefore would be very useful in industry.

SUMMARY OF THE INVENTION

Accordingly, the object of the present invention is to provide a method for inexpensive mass production of geranylgeraniol and analogous compounds thereof using a microorganism capable of producing geranylgeraniol and analogous compounds thereof.

Our research efforts were directed to achieving the above object, and we have performed screening on a wide spectrum of microorganisms, particularly those belonging to identified species, to find yeast cells (ascomycetes and deuteromycetes), bacterial cells, actinomycete cells and filamentous fungus cells capable of producing geranylgeraniol, farnesol and/or nerolidol, thereby finally completing the invention.

Namely, the present invention provides a method for producing geranylgeraniol and/or farnesol, which comprises culturing geranylgeraniol- and/or farnesol-producing cells belonging to any one of the following genera:

Saccharomyces,
Saccharomycopsis,
Saccharomycodes,
Schizosaccharomyces,
Wickerhamia,
Debaryomyces,
Hansenula,
Hanseniaspora,
Lypomyces,
Pichia,
Kloeckera,
Candida,
Zygosaccharomyces,
Ogataea,
Kuraishia,
Komagataella,
Yarrowia,
Williopsis,
Nakazawaea,
Kluyveromyces,
Torulaspora,
Citeromyces,
Waltomyces,
Bacillus,
Staphylococcus,
Pseudomonas,
Micrococcus,
Exiguobacterium,
Mucor,
Ambrosiozyma,
Cystofilobasidium,
Metschnikowia,
Trichosporon,
Xanthophyllomyces,
Bullera,
Fellomyces,

*Filobasidium,*
*Holtermannia,*
*Phaffia,*
*Rhodotorula,*
*Sporidiobolus,*
*Sporobolomyces,*
*Zygoascus,*
*Haloferax,*
*Brevibacterium,*
*Leucosporidium,*
*Myxozyma,*
*Trichosporiella,* and
*Alcaligenes*
in a medium to produce and accumulate geranylgeraniol and/or farnesol in the cells and/or in the extracellular environment; and then collecting geranylgeraniol and/or farnesol.

Also, the present invention provides a method for producing nerolidol, which comprises culturing nerolidol-producing cells belonging to any one of the following genera:
*Saccharomyces,*
*Cryptococcus,*
*Candida,*
*Streptomyces,*
*Nocardia,*
*Cystofilobasidium,*
*Rhodotorula,*
*Willopsis,* and
*Haloferax*
in a medium to produce and accumulate nerolidol in the cells and/or in the extracellular environment; and then collecting nerolidol.

This specification includes part or all of the contents as disclosed in the specification and/or drawings of Japanese Patent Application Nos. 2000-401266 and 2001-376173, which are priority documents of the present application.

BRIEF DESCRIPTION OF THE DRAWINGS

TABLES 1–4 illustrate strains producing geranylgeraniol alone, strains producing both geranylgeraniol and farnesol, strains producing farnesol alone and strains producing nerolidol along, respectively, along with yields thereof.

TABLES 5–6 illustrate the yields of geranylgeraniol and farnesol in three strains, *Hanseniaspora valbyensis* strain IFO 0115, *Saccaromycodies ludwiggi* strain IFO 0339, and *Candida glabrata* strain IFO 0005, in the supernatant fraction and the cell fraction, respectively.

TABLES 7–8 illustrate the production of farnesol and geranylgeraniol in certain strains using YM medium alone or YM medium supplements with 5% glucose and 1% soybean oil, respectively.

TABLES 9–10 illustrate the production of nerolidol, farnesol and gernaylgeraniol in certain strains using YM medium supplemented with 4 mg/L ergosterol and 0–20 mg/L squalene synthesis inhibitor (SQAD) or YM medium supplements with 5% glucose and 1% soybean oil along with 4 mg/L erogosterol and 0–20 mg/L squalene synthesis inhibitor, respectively.

TABLES 11–12 illustrate the production of nerolidol, farnesol and gernaylgeraniol in certain strains using YM medium supplemented with 1% soybean oil, 6% glucose, 4 mg/L ergosterol and 0 mg/L or 20 mg/L squalene synthesis inhibitor (SQAD) in the supernatant fraction and the cell fraction, respectively.

TABLE 13 illustrates the production of nerolidol, geranylgeraniol and farnesol in select bacterial strains using KB medium supplementd with 1% soybean oil, 4 mg/L ergosterol, and 0 mg/L or 20 mg/L squalene synthesis inhibitor (SQAD.

TABLE 14 illustrates the culture conditions and yields of nerolidol, farnesol and geranylgeraniol produced by various bacterial strains.

DETAILED DESCRIPTION OF THE INVENTION

The present invention will be described below in more detail.

In the present invention, a microorganism fermentation method is used to produce geranylgeraniol and analogous compounds thereof. As used herein, analogous compounds of geranylgeraniol refers to geranylgeranyl pyrophosphate and compounds produced in association with the synthesis thereof, i.e., geranylgeranyl monophosphate, farnesyl pyrophosphate, farnesyl monophosphate, farnesol, geranyl pyrophosphate, geranyl monophosphate, geraniol, nerolidol, geranyllinalool, linalool and the like.

In the present invention, any microorganism may be used for geranylgeraniol production, so long as it has the ability to produce geranylgeraniol. Examples include yeast strains belonging to any one of *Saccharomyces, Saccharomycopsis, Saccharomycodes, Schizosaccharomyces, Wickerhamia, Debaryomyces, Hansenula, Hanseniaspora, Pichia, Kloeckera, Candida, Zygosaccharomyces, Ogataea, Kuraishia, Komagataella, Yarrowia, Williopsis, Nakazawaea, Kluyveromyces, Cryptococcus, Torulaspora, Bullera, Rhodotorula, Willopsis, Kloeckera* and *Sporobolomyces;* filamentous fungus strains belonging to *Mucor;* archaebacterial strains belonging to *Haloferax;* or bacterial strains belonging to *Alcaligenes.*

Specific examples of geranylgeraniol-producing cells will be presented below:

(1) *Saccharomyces:*
  *Saccharomyces cerevisiae* strains ATCC 12341, IFO 0565, IFO 0222, IFO 0216, ATCC 9080, IFO 1346, ATCC 204660, IFO 0538 and IFO 0210, *Saccharomyces ellipsoideus* strain 4102 (Kyoto Univ.), *Saccharomyces sake* strain Kyokai No.2, *Saccharomyces rosei* strain IFO 0252, and *Saccharomyces kluyveri* strain IFO 1892;

(2) *Saccharomycopsis:*
  *Saccharomycopsis fibuligera* strains IFO 0106, IFO 1665, IFO 1774 and IFO 0107;

(3) *Saccharomycodes:*
  *Saccharomycodes ludwigii* strain IFO 0339;

(4) *Schizosaccharomyces:*
  *Schizosaccharornyces octosporus* strain IAM 4842 and *Schizosaccharomyces pombe* strain IFO 0346;

(5) *Wickerhamia:*
  *Wickerhamia fluorescens* strain IFO 1116;

(6) *Debaryomyces:*
  *Debaryomyces hansenii* var. *fabryi* strain IFO 0794, *Debaryomyces castellii* strain IFO 1359, and *Debaryomyces vanrijiae* var. *vanrijiae* JCM 2169;

(7) *Hansenula:*
  *Hansenula polymorpha* strain 4327 (Kyoto Univ.);

(8) *Hanseniaspora*:
   *Hanseniaspora valbyensis* strain IFO 0115;
(9) *Pichia*:
   *Pichia membranaefaciens* strain IFO 0128, *Pichia aganobii* strain 4261 (Kyoto Univ.), *Pichia naganishii* strain IFO 1670, *Pichia silvicola* strain IFO 0807, and *Pichia anomala* strains IFO 0118, IFO 0569 and IFO 0707;
(10) *Kloeckera*:
   *Kloeckera japonica* strain IFO 0151;
(11) *Candida*:
   *Candida krusei* strain IFO 0013, *Candida kefyr* strain IFO 0706, *Candida tenuis* strain IFO 0716, *Candida solani* strain IFO 0762, *Candida glabrata* strains IFO 0005 and IFO 0622, *Candida albicans* strain IFO 1060, *Candida zeylanoides* strain IFO 0719, *Candida catenulata* strain IFO 0720, *Candida cariosilignicola* strain IFO 1910, *Candida stellata* strain IFO 0701, and *Candida utilis* strain IFO 0619;
(12) *Zygosaccharomyces*:
   *Zygosaccharomyces rouxii* strain IFO 0487, and *Zygosaccharomyces japanicus* strain IFO 0595;
(13) *Ogataea*:
   *Ogataea glucozyma* strain IFO 1472, and *Ogataea polymorpha* strain IFO 1475;
(14) *Kuraishia*:
   *Kuraishia capsulata* strain IFO 0974;
(15) *Komagataella*:
   *Komagataella pastoris* strain IFO 0948;
(16) *Yarrowia*:
   *Yarrowia lopolytica* strain IFO 0717;
(17) *Williopsis*:
   *Williopsis saturnus* var. *saturnus* strains IFO 0125 and IFO 0941, and *Williopsis saturnus* strain IFO 0895;
(18) *Nakazawaea*:
   *Nakazawaea holstii* strain IFO 0980;
(19) *Kluyveromyces*:
   *Kluyveromyces marxianus* strains IFO 0617 and IFO 0288, *Kluyveromyces thermotolerans* strain IFO 0662, and *Kluyveromyces lactis* strain IFO 0648;
(20) *Torulaspora*:
   *Torulaspora delbrueckii* strain IFO 0422;
(21) *Cryptococcus*:
   *Cryptococcus humicolus* strain IFO 1527; and
(22) *Mucor*:
   *Mucor javanicus* strain IFO 4570;
(23) *Bullera*:
   *Bullera pseudoalba* strain IFO 10179;
(24) *Rhodotorula*:
   *Rhodotorula minuta* strain IFO 0715, and *Rhodotorula rubra* strain IFO 0870;
(25) *Sporobolomyces*:
   *Sporobolomyces salmonicolor* strain IFO 0374;
(26) *Haloferax*:
   *Haloferax volcanii* strain IFO 14742; and
(27) *Alcaligenes*:
   *Alcaligenes faecalis* strain IFO 13111.

In the present invention, any microorganism may be used for farnesol production, so long as it has the ability to produce farnesol. Examples include yeast strains belonging to any one of *Saccharomyces, Saccharomycopsis, Saccharomycodes, Schizosaccharomyces, Wickerhamia, Debaryomyces, Hanseniaspora, Lypomyces, Pichia, Candida, Ogataea, Kuraishia, Komagataella, Yarrowia, Kluyveromyces, Torulaspora, Zygosaccharomyces, Williopsis, Citeromyces, Waltomyces* and *Cryptococcus*; bacterial strains belonging to any one of *Bacillus, Staphylococcus, Pseudomonas, Micrococcus* and *Exiguobacterium*; filamentous fungus strains belonging to *Mucor*; or microbial strains belonging to any one of *Ambrosiozyma, Cystofilobasidium, Metschnikowia, Trichosporon, Xanthophyllomyces, Bullera, Fellomyces, Filobasidium, Holtermannia, Phaffia, Sporidiobolus, Sporobolomyces, Zygoascus, Leucosporidium, Myxozyma, Trichosporiella, Haloferax* and *Brevibacterium*.

Specific examples of farnesol-producing cells will be presented below:
(1) *Saccharomyces*:
   *Saccharomyces cerevisiae* strains IFO 1346, ATCC 204660, IFO 0258, IFO 0262, IFO 0538, IFO 0565, IFO 0210 and IFO 2347, *Saccharomyces unisporus* strain IFO 0215, *Saccharomyces sake* strain Kyokai No.2, *Saccharomyces ellipsoideus* strain 4102 (Kyoto Univ.), *Saccharomyces rosei* strain IFO 0252, *Saccharomyces logos* strain 4101 (Kyoto Univ.), *Saccharomyces dairensis* strain IFO 0285, *Saccharomyces bayanus* strains IFO 0539 and IFO 0613, *Saccharomyces kluyveri* strain IFO 1892, and *Saccharomyces paradoxus* strain IFO 0259;
(2) *Saccharomycodes*:
   *Saccharomycodes ludwigii* strain IFO 0339;
(3) *Schizosaccharomyces*:
   *Schizosaccharomyces pombe* strains IFO 0346, IFO 0638 and IFO 0358, and *Schizosaccharomyces octosporus* strain IAM 4842;
(4) *Hanseniaspora*:
   *Hanseniaspora valbyensis* strain IFO 0115;
(5) *Debaryomyces*:
   *Debaryomyces hansenii* strain IFO 0023, *Debaryomyces hansenii* var. *fabryi* strain IFO 0749, *Debaryomyces castellii* strain IFO 1359, and *Debaryomyces vanrijiae* var. *vanrijiae* strain JCM 2169;
(6) *Lypomyces*:
   *Lypomyces starkeyi* strain IFO 0678;
(7) *Pichia*:
   *Pichia aganobii* strain 4261 (Kyoto Univ.), *Pichia naganishii* strain IFO 1670, and *Pichia anomala* strains IFO 0118, IFO 0569, IFO 0963, IFO 707 and IFO 0146;
(8) *Candida*:
   *Candida utilis* strains IFO 0626 and IFO 0619, *Candida albicans* strains IFO 0579 and IFO 1060, *Candida zeylanoides* strain IFO 0719, *Candida glabrata* strains IFO 0005, IFO 0622 and IFO 0741, *Candida cariosilignicola* strain IFO 1910, *Candida stellata* strain IFO 0701, *Candida solani* strain IFO 0762, *Candida intermedia* strain IFO 0761, *Candida krusei* strain IFO 0941 and *Candida tenuis* strain IFO 0716;
(9) *Wickerhamia*:
   *Wickerhamia fluoresces* strain IFO 1116;
(10) *Kuraishia*:
   *Kuraishia capsulata* strain IFO 0974;
(11) *Komagataella*:
   *Komagataella pastoris* strain IFO 0948;
(12) *Ogataea*:
   *Ogataea glucozyma* strain IFO 1472 and *Ogataea polymorpha* strain IFO 1475;
(13) *Yarrowia*:
   *Yarrowia lopolytica* strain IFO 0717;
(14) *Kluyveromyces*:
   *Kluyveromyces marxianus* strains IFO 0288 and IFO 0617, *Kluyveromyces thermotolerans* strain IFO 0662, and *Kluyveromyces lactis* strain IFO 0648;

(15) *Torulaspora:*
  *Torulaspora delbrueckii* strain IFO 0422;
(16) *Zygosaccharomyces:*
  *Zygosaccharomyces rouxii* strains IFO 0487 and IFO 0686, *Zygosaccharomyces japanicus* strain IFO 0595, and *Zygosaccharomyces fermentati* strain IFO 0021;
(17) *Williopsis:*
  *Williopsis saturnus* var. *saturnus* strain IFO 0941, *Williopsis californica* strain IFO 0800 and *Willopsis saturnus* strain IFO 0895;
(18) *Citeromyces:*
  *Citeromyces matritensis* strain IFO 0954;
(19) *Waltomyces:*
  *Waltomyces lipoder* strain IFO 0673;
(20) *Cryptococcus:*
  *Cryptococcus humicolus* strain IFO 1527;
(21) *Bacillus:*
  *Bacillus amyloliquefaciens* strain IFO 3022 and *Bacillus pumilus* IFO 3030
(22) *Staphylococcus:*
  *Staphylococcus epidermidis* strain IFO 3762;
(23) *Pseudomonas:*
  *Pseudomonas sp.* strain 876 (Kyoto Univ.);
(24) *Micrococcus:*
  *Micrococcus luteus* strain IFO 3067;
(25) *Exiguobacterium:*
  *Exiguobacterium acetylicum* strain IFO 12146;
(26) *Mucor:*
  *Mucor javanicus* strain IFO 4570;
(27) *Ambrosiozyma:*
  *Ambrosiozyma platypodis* strain IFO 10752;
(28) *Cystofilobasidium:*
  *Cystofilobasidium infirmominiatum* strain IFO 1057;
(29) *Leucosporidium:*
  *Leucosporidium scottii* strain IFO 1924;
(30) *Metschnikowia:*
  *Metschnikowia lunata* strain IFO 1605;
(31) *Myxozyma:*
  *Myxozyma lipomycoides* strain IFO 10351;
(32) *Trichosporon:*
  *Trichosporon pullulans* strain IFO 1232;
(33) *Xanthophyllomyces:*
  *Xanthophyllomyces dendrorhous* strain IFO 10130;
(34) *Bullera:*
  *Bullera pseudoalba* strain IFO 10179;
(35) *Fellomyces:*
  *Fellomyces penicillatus* strain IFO 10119;
(36) *Filobasidium:*
  *Filobasidium capsuligenum* strain IFO 1185, and *Filobasidium uniguttulatum* strain IFO 0699;
(37) *Kloeckera:*
  *Kloeckera corticis* strain IFO 0633;
(38) *Holtermannia:*
  *Holtermannia corniformis* strain IFO 10742;
(39) *Phaffia:*
  *Phaffia rhodozyma* strain ATCC 66270;
(40) *Saccharomycopsis:*
  *Saccharomycopsis fermentans* strain IFO 10772;
(41) *Sporidiobolus:*
  *Sporidiobolus samonicolar* strain IFO 1035;
(42) *Sporobolomyces:*
  *Sporobolomyces salmonicolor* strain IFO 0374;
(43) *Trichosporiella:*
  *Trichosporiella flavificans* strain IFO 1573;
(44) *Zygoascus:*
  *Zygoascus hellenicus* strain IFO 10184;
(45) *Haloferax:*
  *Haloferax volcanii* strain IFO 14742; and
(46) *Brevibacterium:*
  *Brevibacterium linens* strain IFO 12171.

In the present invention, any microorganism may be used for nerolidol production, so long as it has the ability to produce nerolidol. Examples include yeast strains belonging to *Saccharomyces*, *Candida* or *Cryptococcus*; actinomycete strains belonging to *Streptomyces* or *Nocardia*; or microbial strains belonging to any one of *Cystofilobasidium*, *Rhodotorula*, *Willopsis* and *Haloferax*.

Specific examples of nerolidol-producing cells will be presented below:
(1) *Nocardia:*
  *Nocardia asteroides* strain IFO 3384 and *Nocardia fusca* strain IFO 14340;
(2) *Streptomyces:*
  *Streptomyces gardneri* strain IFO 12865;
(3) *Saccharomyces:*
  *Saccharomyces unisporus* strain IFO 0215, *Saccharomyces cerevisiae* strain IFO 0210, and *Saccharomyces ellipsoideus* strain 4102 (Kyoto Univ.);
(4) *Candida:*
  *Candida glabrata* strains IFO 0005 and IFO 0741, *Candida solani* strain IFO 0762, and *Candida krusei* strain IFO 0941;
(5) *Cryptococcus:*
  *Cryptococcus humicolus* strain IFO 1527;
(6) *Cystofilobasidium:*
  *Cystofilobasidium infirmominiatum* strain IFO 1057;
(7) *Rhodotorula:*
  *Rhodotorula minuta* strain IFO 0715, and *Rhodotorula rubra* strain IFO 0870;
(8) *Willopsis:*
  *Williopsis californica* strain IFO 0800; and
(9) *Haloferax:*
  *Haloferax volcanii* strain IFO 14742.

In addition to the above-listed microorganisms, further examples of microorganisms capable of producing geranylgeraniol, farnesol and/or nerolidol, which can be used in the present invention, include microbial strains belonging to any one of *Dipodascus*, *Issatchenkia*, *Mortierella*, *Rhodosporidium*, *Tsukamurella*, *Yamadazyma*, *Bensingtonia*, *Botryozyma*, *Brettanomyces*, *Clavispora*, *Dekkera*, *Eremascus*, *Eremothecium*, *Erythrobasidium*, *Kloeckeraspora*, *Kockovaella*, *Kodamaea*, *Kurtzmanomyces*, *Lodderomyces*, *Malassezia*, *Mrakia*, *Nadsonia*, *Pachysolen*, *Saturnispora*, *Schizoblastosporion*, *Sporopachydermia*, *Stephanoascus*, *Sterigmatomyces*, *Sterigmatosporidium*, *Sympodiomyces*, *Sympodiomycopsis*, *Trigonopsis*, *Tsuchiyaea*, *Zygozyma* and *Aciculoconidium*.

Culture of the microorganisms used in the present invention will be described in turn. In general, any medium may be used to culture the microorganisms, so long as it allows the growth of these microorganisms. Specific examples include YM medium, KY medium and F101 medium for culture of yeast cells (ascomycetes and deuteromycetes); and KB medium for culture of bacterial cells and actinomycete cells.

Any carbon compound may be used as a carbon source, so long as the microorganisms can assimilate it for growth.

As a nitrogen source, for example, an inorganic nitrogen source including ammonium sulfate, ammonium chloride or ammonium nitrate, or an organic nitrogen source including yeast extract, peptone or meat extract may be used. In addition to these, a medium may further contain minerals, metal salts, and/or vitamins, if necessary.

Culture conditions will vary depending on the types of microorganisms. In general, the culture may preferably be performed at a temperature of 20° C. to 40° C., more preferably 25° C. to 35° C., and at a pH of 5 to 9. The culture may also be performed under anaerobic or aerobic conditions according to the types of microorganisms, preferably performed under aerobic conditions with shaking or rotating because aerobic conditions permit a higher growth speed than anaerobic conditions.

However, it is naturally important to select culture conditions for maximum production of geranylgeraniol and analogous compounds thereof, according to the type of microorganism to be used and the composition of the medium.

To improve production of geranylgeraniol and analogous compounds thereof (hereinafter, collectively referred to as "geranylgeraniol analogs") and to stimulate product secretion from cells, a medium may be supplemented with a sugar and/or a fat or oil.

Examples of a sugar able to be used in the present invention include glucose, sucrose and the like. Examples of a fat or oil able to be used in the present invention include soybean oil, fish oil, almond oil, olive oil and the like.

For example, a sugar may be added to a medium at a concentration of 1% to 10%, preferably 2% to 7%, while a fat or oil may be added to a medium at a concentration of 0.01% or more, preferably 1% or more. As used herein, the percentage (%) used to express a sugar content etc. is based on w/v (%).

A medium may further be supplemented with ergosterol along with a squalene synthase inhibitor in order to give a further improvement in production of geranylgeraniol analogs. Examples of a squalene synthase inhibitor include BSM-187745 (Toxicology and applied pharmacology 145, 91–98 (1987)), SQAD(Japanese patent Application No.8-508245) and zaragozic acid. The squalene synthase inhibitor may be used at a concentration of 1 mg/L to 20 mg/L.

In the present invention, geranylgeraniol analogs may be produced in a batch manner or in a continuous manner using a bioreactor. Microorganism cells may be provided as such for geranylgeraniol analog production or may be pre-treated to give crushed cells, a culture solution, a crude enzyme, or a purified enzyme. Cultured cells or these pre-treated products may also be immobilized by an immobilization technique. The cells or pre-treated products are cultured to produce and accumulate geranylgeraniol analogs in the cells or culture supernatant, which are then collected.

To collect geranylgeraniol analogs from a culture supernatant fraction, a supernatant from which cells have been removed by centrifugation is treated with alkaline phosphatase in a buffer containing magnesium chloride, and then extracted with a solvent such as pentane or methanol.

To collect geranylgeraniol analogs from a cultured cell fraction, on the other hand, the cells collected by centrifugation are crushed, treated with alkaline phosphatase in a buffer containing magnesium chloride, and then extracted with a solvent such as pentane or methanol.

The above solvent extraction step may be performed in combination with a known purification technique such as chromatography, as needed.

The use of alkaline phosphatase in the extraction step is effective in improving farnesol and geranylgeraniol production because it allows hydrolysis of farnesyl pyrophosphate and geranylgeranyl pyrophosphate present as precursors for farnesol and geranylgeraniol in the cells or culture solution. A preferred phosphatase is alkaline phosphatase derived from *E. coli*, but other phosphatases including potato-derived acid phosphatase or calf intestine phosphatase may also be used. Since most microorganisms possess an endogenous phosphatase, the organic solvent extraction step may also be performed without phosphatase treatment, although a slight decrease in production is observed.

In the production method of the present invention, geranylgeraniol analogs are detected by gas chromatography/mass spectrometry (GC/MS) using a commercially available column and then quantified from the ratio of peak area between each analog and 1-undecanol as an internal standard.

EXAMPLES

The present invention will be further described in the following examples. The examples are provided for illustrative purposes only, and are not intended to limit the scope of the invention.

Example 1

Screening of Geranylgeraniol Analog-producing Cells (1) Strain

Screening was performed on about 930 strains purchased from ATCC, IAM, IFO and JCM as well as provided by Professor Shimizu (Kyoto University, Japan) to find geranylgeraniol analog-producing cells.

(2) Strain Storage

Strains were stored appropriately in the following three ways.

(i) Glycerol Stocks

300 μl of autoclaved 50% glycerol (Nacalai) was added to 900 μl of a liquid culture solution and then stored at −80° C. and −20° C. A strain stored at −20° C. was plated after one week to confirm that the storage was succeeded.

(ii) Lyophilized Stocks 2 ml of a liquid culture solution was transferred to a 2 ml Eppendorf tube and then centrifuged at 6000 rpm for 5 minutes to collect cells. The cells were suspended in 150 μl of 20% skim milk (Morinaga Milk Industry Co., Ltd.) solution autoclaved at 110° C. for 20 minutes. The suspension was transferred to a glass tube for lyophilization using a dry-sterilized Pasteur pipette and then frozen in a freezer at −80° C. After sufficiently drying overnight in a lyophilizer (Lyph Lock 1L; Labconco), the glass tube was sealed using a band burner GB20001 (Prince). A Tesler coil (model WTC-100; Wakaida Science Corporation) was used to confirm whether sealing had succeeded.

(iii) Paraffin-Overlaid Stocks

A 2% agar slant having the same composition as that of a liquid medium was prepared. Cells were streaked from a liquid culture solution onto the slant by using a disposable loop. The slant was allowed to stand at room temperature for one week. The slant confirmed to show sufficient cell growth was overlaid with autoclaved liquid paraffin (Nacalai) at a depth of about 1 cm and stored at 4° C.

(3) Preparation of Liquid Medium

Yeast cells were cultured in YM medium (Difco), or KY or F101 medium prepared as presented below. Bacterial cells or actinomycete cells were cultured in KB medium.

A plate was prepared from the same medium by addition of Bactoagar (Difco) at a final concentration of 2%.

KY Medium

The following ingredients were added to 1 L of deionized water, adjusted to pH 5.5 with 2N sodium hydroxide, and then adjusted to 1 L with deionized water, followed by autoclaving.

| | |
|---|---|
| Malt Extract (Difco) | 5 g |
| Yeast Extract (Difco) | 5 g |

F101 Medium 200 g of diced potato was introduced into 500 ml of deionized water, boiled for 30 minutes and then filtered through gauze to remove an insoluble residue. The following ingredients were added to the resulting solution, and then adjusted to 1 L with deionized water, followed by autoclaving.

| | |
|---|---|
| Yeast Extract (Difco) | 30 g |
| Glucose (Nacalai) | 15 g |
| Sucrose (Nacalai) | 15 g |

KB Medium

The following ingredients were added to 1 L of deionized water, adjusted to pH 7.0 with 2N potassium hydroxide, and then adjusted to 1 L with deionized water, followed by autoclaving.

| | |
|---|---|
| Bactotryptone (Difco) | 5 g |
| Yeast Extract (Difco) | 5 g |
| Glucose (Nacalai) | 1 g |
| $KH_2PO_4$ (Nacalai) | 0.7 g |
| $K_2HPO_4$ (Nacalai) | 0.3 g |

(4) Liquid Culture

Each medium (20 ml) prepared above was separately introduced into a 100 ml baffled Erlenmeyer flask, which was then closed with a Morton closure and autoclaved at 121° C. and at 1.2 atm for 15 minutes. A loopful of cells was inoculated from the slant into the autoclaved media and then cultured at 30° C. for 3 days while rotating at 130 rpm.

(5) Extraction of Geranylgeraniol Analogs from Supernatant Fraction 2.5 ml of the culture solution was transferred into a test tube ($\phi$18 mm×125 mm), and centrifuged in a Beckman centrifuge GP at 1000 rpm for 5 minutes to give the supernatant, which was then transferred to another new test tube ($\phi$18 mm×125 mm). 0.5 ml of Tris-HCl buffer (pH 8.0) containing 6 mM magnesium chloride and 5 $\mu$l (2 units) of E. coli alkaline phosphatase (Takara Shuzo Co., Ltd.) were added to the supernatant and heated to 65° C. for 30 minutes. After sufficiently cooling on ice, the treated supernatant was mixed well with 2 ml of pentane and 1 ml of methanol, and centrifuged in a Beckman centrifuge GP at 1000 rpm for 5 minutes to give the supernatant, which was then transferred to another new test tube. After evaporation of pentane and methanol in a draft chamber, the resulting residue was re-dissolved in 300 ml of pentane and filled into a vial for GC/MS.

(6) Extraction of Geranylgeraniol Analogs from Cell Fraction (i) Extraction from Bacterial and Actinomycete Cells 10 ml of the liquid culture solution was transferred into a 50 ml Corning tube and centrifuged in a Beckman refrigerated centrifuge (Avant J25-I) at 6000 rpm for 5 minutes to collect the cells. After the cells were suspended in 0.5 ml of deionized water, the suspension was transferred into a 10 ml conical bottom tube and crushed using an ultrasonic vibrator UC W-201 (Tokai electric Inc.) at 10° C. for 20 minutes by repeating the following cycle: crushing for 1 minute and allowing to rest for 30 seconds. The crushed cells were transferred into a test tube ($\phi$18 mm×125 mm) and mixed with 0.5 ml of Tris-HCl buffer (pH 8.0) containing 6 mM magnesium chloride, followed by phosphatase treatment and extraction as in (5) above.

(ii) Extraction from Yeast Cells 2.5 ml of the liquid culture solution was transferred into a test tube ($\phi$18 mm×125 mm) and centrifuged in a Beckman centrifuge GP at 1000 rpm for 5 minutes to collect the cells. After the cells were suspended in 0.5 ml of Tris-HCl buffer (pH 8.0) containing 6 mM magnesium chloride, the suspension was transferred into a glass tube for crushing. An equal volume of glass beads (Sigma; acid washed$\phi$+=425–600 $\mu$m) was added to the tube and the cells were crushed using a Multi-Beads Schocker MB-200 (YASUI KIKAI) at 2500 rpm and at room temperature for 20 minutes. The whole content of the glass tube was transferred into a test tube ($\phi$18 mm×125 mm), followed by phosphatase treatment and extraction as in (5) above.

(7) Analysis of Geranylgeraniol Analogs

Analysis was performed using an Agilent HP6890/5973 GC/MS system under the following conditions:

| | |
|---|---|
| i) Inlet temperature: | 250° C. |
| ii) Detector temperature: | 260° C. |
| iii) MS zone temperatures: | |
| MS Quad: | 150° C. |
| MS Source: | 230° C. |
| iv) Scan parameters: | |
| Low Mass: | 35 |
| High Mass: | 200 |
| Threshold: | 40 |
| v) Injection parameters: | |
| Mode: | automatic injection |
| Sample volume: | 2 $\mu$l |
| Washing: | 3 times with methanol and twice with hexane |
| Split ratio: | 1:20 |
| Column: | Agilent HP-5MS (0.25 mm × 30 m; film thickness of 0.25 $\mu$m) |
| Carrier gas: | helium at 1.0 ml/min |
| Solvent delay: | 2 minutes |
| Oven conditions: | holding at 115° C. for 1.5 minutes heating to 250° C. at 70° C./min, holding for 2 minutes heating to 300° C. at 70° C./min, holding for 7 minutes post time = 0 |
| Internal standard: | 1-undecanol/ethanol solution (1 $\mu$l/ml), added to each vial in an amount of 10 $\mu$l |
| Inlet liner: | split/splitless liners |
| Analysis: | After incorporation of TIC, 69 mass was selected to integrate the peak area for each of 1-undecanol (RT = 3.39 min), nerolidol (RT = 3.86 min), farnesol (RT = 4.23 min) and geranylgeraniol (RT = 5.78 min). Each substance was quantified from the ratio of peak area between the substance and undecanol as an internal standard. |

(8) Results

Among screened strains, about one-third of 162 ascomycete strains and about one-tenth of 73 deuteromycete strains were confirmed to produce geranylgeraniol and/or farnesol, while three of 95 actinomycete strains were confirmed to produce nerolidol.

Tables 1, 2, 3 and 4 illustrate strains producing geranylgeraniol alone, strains producing both geranylgeraniol and farnesol, strains producing farnesol alone and strains producing nerolidol alone, respectively, along with yields thereof.

Example 2

Examination of Culture Conditions

Examination was performed on the following three strains: the two stains found to provide the highest production of geranylgeraniol in Example 1, *Hanseniaspora valbyensis* strain IFO 0115 and *Saccharomycodes ludwigii* strain IFO 0339, and *Candida glabrata* strain IFO 0005 found to provide high production of both geranylgeraniol and farnesol in Example 1. The results, including days of culture, medium composition, and changes in production with or without phosphatase treatment, are shown in Table 5 (supernatant fraction) and Table 6 (cell fraction). Each strain produces more farnesol and geranylgeraniol over the course of time. The addition of 5% glucose to the medium permits an increased production in the cell fraction. Further, the addition of 1% soybean oil along with glucose stimulates *Candida glabrata* strain to secrete farnesol and geranylgeraniol from the cells. Thus, although some differences are found among microorganisms, the use of the medium supplemented with 5% glucose and 1% soybean oil enables more farnesol and geranylgeraniol to be produced in and secreted from the cells.

Also, the supernatant fraction tends to contain more farnesol and geranylgeraniol in the absence of phosphatase treatment, whereas the cell fraction tends to contain more farnesol and geranylgeraniol when treated with phosphatase, thereby suggesting that farnesyl pyrophosphate and geranyl pyrophosphate are present in the cell fraction.

Example 3

Examination of Culture Conditions

Some of the strains tested in Example 1 were cultured in YM medium alone and in YM medium supplemented with 5% glucose and 1% soybean oil to examine farnesol and geranylgeraniol production. Tables 7 and 8 show the results obtained. The medium supplemented with 5% glucose and 1% soybean oil effected a significantly increased production.

Example 4

Examination of Culture Conditions

Each of the strains shown in Tables 9 and 10 was cultured in YM medium supplemented with 4 mg/L ergosterol and 0–20 mg/L squalene synthesis inhibitor (SQAD) or in YM medium supplemented with 5% glucose and 1% soybean oil along with 4 mg/L ergosterol and 0–20 mg/L squalene synthesis inhibitor (SQAD) to examine the respective production of nerolidol, geranylgeraniol and farnesol in the same manner as stated above. Tables 9 and 10 also show the results obtained.

Further, each of the strains shown in Tables 11 and 12 was cultured in YM medium supplemented with 1% soybean oil, 6% glucose, 4 mg/L ergosterol, and 0 mg/L or 20 mg/L squalene synthesis inhibitor (SQAD) to examine the respective production of nerolidol, geranylgeraniol and farnesol in the same manner as stated above. The results are shown in Table 11 (supernatant fraction) and Table 12 (cell fraction).

These tables indicate that the addition of soybean oil, glucose and a squalene synthesis inhibitor effects an increased production.

Example 5

Examination of Culture Medium Conditions

Each bacterial strain detected to produce farnesol was cultured in KB medium supplemented with 1% soybean oil, 4 mg/L ergosterol, and 0 mg/L or 20 mg/L squalene synthesis inhibitor (SQAD) to examine the respective production of nerolidol, geranylgeraniol and farnesol in the same manner as stated above. Table 13 shows the results obtained. This table indicates that the addition of a squalene synthesis inhibitor effects an increased production in bacterial strains as in the case of yeast strains.

Example 6

Under the culture conditions shown in Table 14 (e.g., days of culture, culture temperature, type of medium), various strains were cultured according to the same culture procedures as described in Example 1, followed by extraction of geranylgeraniol analogs from both cell and supernatant fractions. Analysis was performed on these fractions. Table 14 also shows the results obtained. LBO-SSI, YPDO-SSI, YMO-SSI, YMOL-SSI and HVO-SSI media used in this example were prepared as follows.

LBO-SSI Medium

The following ingredients were dissolved in 1 L of deionized water and then autoclaved. After the autoclaved medium was fully cooled, a filter-sterilized aqueous solution of squalene synthase inhibitor SQAD (2.5 mg/ml) was added to the medium to give a final concentration of 20 mg/L.

| | |
|---|---|
| Yeast Extract (Difco) | 5 g |
| Bactopeptone (Difco) | 10 g |
| NaCl (Nacalai) | 5 g |
| Glucose (Nacalai) | 50 g |
| Soybean oil (Nacalai) | 10 ml |
| Ergosterol solution | 200 µl (200 µl of 20 mg/ml solution in 50% EtOH-50% Tergitol) |

YPDO-SSI Medium

The following ingredients were dissolved in 1 L of deionized water and then autoclaved. After the autoclaved medium was fully cooled, a filter-sterilized aqueous solution of squalene synthase inhibitor SQAD (2.5 mg/ml) was added to the medium to give a final concentration of 20 mg/L.

| | |
|---|---|
| Yeast Extract (Difco) | 10 g |
| Bactopeptone (Difco) | 20 g |
| Glucose (Nacalai) | 50 g |
| Soybean oil (Nacalai) | 10 ml |
| Ergosterol solution | 200 µl (200 µl of 20 mg/ml solution in 50% EtOH-50% Tergitol) |

YMO-SSI Medium

The following ingredients were added to YM medium (Difco), adjusted to 1 L with deionized water and then autoclaved. After the autoclaved medium was fully cooled, a filter-sterilized aqueous solution of squalene synthase inhibitor SQAD (2.5 mg/ml; Ltd.) was added to the medium to give a final concentration of 1 to 20 mg/L.

| | |
|---|---|
| Glucose (Nacalai) | 50 g |
| Soybean oil (Nacalai) | 10 ml |
| Ergosterol (Nacalai) | 4 mg (200 µl of 20 mg/ml solution in 50% EtOH-50% Tergitol) |

YMOL-SSI Medium

This medium was prepared by adding 10 ml of olive oil (Nacalai) to YMO medium in the same manner as used for YMO-SSI preparation.

HVO-SSI Medium

The following ingredients were dissolved in 1 L of deionized water and then autoclaved. After the autoclaved medium was fully cooled, a filter-sterilized aqueous solution of squalene synthase inhibitor SQAD (2.5 mg/ml) was added to the medium to give a final concentration of 20 mg/L.

| | |
|---|---|
| NaCl (Nacalai) | 156 g |
| $MgCl_2 \cdot 6H_2O$ (Nacalai) | 13 g |
| $MgSO_4 \cdot 7H_2O$ (Nacalai) | 20 g |
| $CaCl_2 \cdot 2H_2O$ (Nacalai) | 1 g |
| KCl (Nacalai) | 4 g |
| $NaHCO_3$ (Nacalai) | 0.2 g |
| KBr (Nacalai) | 0.5 g |
| Yeast Extract (Difco) | 5 g |
| Glucose (Nacalai) | 50 g |
| Soybean oil (Nacalai) | 10 ml |
| Ergosterol solution | 200 µl (200 µl of 20 mg/ml solution in 50% EtOH-50% Tergitol) |

The present invention enables inexpensive mass production of geranylgeraniol and analogous compounds thereof by using microorganisms capable of producing geranylgeraniol, farnesol and/or nerolidol useful as biosynthetic intermediates of terpenes, carotenoids and/or steroids.

All publications, patents and patent applications cited herein are incorporated herein by reference in their entirety.

TABLE 1

| Strains | | Supernatant fraction (µg/L of culture solution) | | Cell fraction (µg/L of culture solution) | |
|---|---|---|---|---|---|
| Strain No. | Genus | FOH | GGOH | FOH | GGOH |
| ATCC 12341 | Saccharomyces cerevisiae | 0.0 | 0.0 | 0.0 | 14.4 |
| K 4010 | Saccharomyces sp. | 0.0 | 0.0 | 0.0 | 9.1 |
| K 4031 | Saccharomyces sp. | 0.0 | 0.0 | 0.0 | 7.0 |
| K 4037 | Saccharomyces sp. | 0.0 | 0.0 | 0.0 | 5.8 |
| K 4039 | Saccharomyces sp. | 0.0 | 0.0 | 0.0 | 5.5 |
| K 4041 | Saccharomyces sp. | 0.0 | 0.0 | 0.0 | 8.4 |
| IFO 0565 | Saccharomyces cerevisiae | 0.0 | 0.0 | 0.0 | 54.7 |
| IFO 0222 | Saccharomyces cerevisiae | 0.0 | 0.0 | 0.0 | 3.3 |
| IFO 0216 | Saccharomyces cerevisiae | 0.0 | 0.0 | 0.0 | 5.8 |
| ATCC 9080 | Saccharomyces cerevisiae | 0.0 | 0.0 | 0.0 | 5.7 |
| IFO 0106 | Saccharomycopsis fibuligera | 0.0 | 0.0 | 0.0 | 3.4 |
| IFO 0125 | Williopsis saturnus var. saturuns | 0.0 | 0.0 | 0.0 | 5.4 |
| IFO 0807 | Pichia silvicola | 0.0 | 0.0 | 0.0 | 1.2 |
| IFO 0980 | Nakazawaea holstii | 0.0 | 0.0 | 0.0 | 5.2 |
| K 4327 | Hansenula polymopla | 0.0 | 0.0 | 0.0 | 4.7 |
| IFO 0151 | Kloeckera japonica | 0.0 | 0.0 | 0.0 | 10.2 |
| IFO 0128 | Pichia membranaefaciens | 0.0 | 0.0 | 0.0 | 11.0 |
| K 4261 | Pichia aganobii | 0.0 | 4.0 | 0.0 | 0.0 |
| IFO 0941 | Williopsis saturnus var. saturuns | 0.0 | 0.0 | 0.0 | 6.7 |
| IFO 0013 | Candida krusei | 0.0 | 0.0 | 0.0 | 16.5 |
| IFO 0706 | Candida kefyr | 0.0 | 0.0 | 0.0 | 4.9 |
| IFO 0716 | Candida tenuis | 0.0 | 0.0 | 0.0 | 8.7 |
| IFO 0617 | Kluyveromyces marxianus | 0.0 | 0.0 | 0.0 | 25.2 |
| IFO 0762 | Candida solani | 0.0 | 0.0 | 0.0 | 29.0 |
| IFO 1060 | Candida albicans | 0.0 | 2.4 | 0.0 | 0.0 |
| IFO 0720 | Candida catenulata | 0.0 | 0.0 | 0.0 | 25.9 |

K: strain maintained by Kyoto University
FOH: farnesol
GGOH: geranylgeraniol

TABLE 2

| Strains | | Supernatant fraction (µg/L of culture solution) | | Cell fraction (µg/L of culture solution) | |
|---|---|---|---|---|---|
| Strain No. | Genus | FOH | GGOH | FOH | GGOH |
| K 4002 | Saccharomyces sp. | 4.4 | 0.0 | 0.0 | 10.9 |
| K 4006 | Saccharomyces sp. | 4.2 | 0.0 | 4.3 | 6.7 |
| K 4013 | Saccharomyces sake | 0.0 | 0.0 | 7.3 | 5.0 |
| K 4015 | Saccharomyces sake | 7.9 | 0.0 | 6.6 | 7.9 |
| K 4016 | Saccharomyces sake | 4.5 | 0.0 | 2.2 | 6.5 |
| K 4017 | Saccharomyces sake | 4.3 | 0.0 | 7.9 | 7.9 |
| K 4018 | Saccharomyces sake | 4.4 | 0.0 | 5.0 | 9.9 |
| K 4020 | Saccharomyces sake | 0.0 | 0.0 | 2.8 | 5.4 |
| K 4022 | Saccharomyces sake | 0.0 | 0.0 | 2.1 | 4.7 |
| K 4023 | Saccharomyces sake | 0.0 | 0.0 | 5.2 | 11.5 |
| K 4025 | Saccharomyces sake | 5.0 | 0.0 | 5.5 | 2.0 |
| K 4026 | Saccharomyces sake | 0.0 | 0.0 | 2.6 | 7.6 |
| K 4029 | Saccharomyces sake | 0.0 | 0.0 | 2.2 | 2.3 |
| K 4030 | Saccharomyces sp. | 5.1 | 0.0 | 4.6 | 3.7 |
| K 4036 | Saccharomyces sp. | 0.0 | 0.0 | 4.1 | 15.2 |
| K 4045 | Saccharomyces cerevisiae | 0.0 | 0.0 | 44.9 | 18.6 |
| K 4102 | Saccharomyces ellipsoideus | 0.0 | 0.0 | 22.9 | 7.2 |
| K 4103 | Saccharomyces cerevisiae | 0.0 | 0.0 | 22.6 | 8.6 |
| K 4104 | Saccharomyces cerevisiae | 0.0 | 0.0 | 15.8 | 31.7 |
| IFO 0252 | Saccharomyces rosei | 0.0 | 0.0 | 28.5 | 39.0 |
| IFO 0288 | Kluyveromyces marxianus | 0.0 | 0.0 | 11.3 | 22.6 |
| Kyokai No. 2 | Saccharomyces sake | 0.0 | 0.0 | 9.7 | 26.1 |
| IFO 0422 | Torulaspora delbrueckii | 0.0 | 0.0 | 8.2 | 11.9 |
| IFO 0487 | Zygosaccharomyces rouxii | 0.0 | 0.0 | 4.9 | 14.3 |
| IFO 1346 | Saccharomyces cerevisiae | 0.0 | 0.0 | 4.3 | 13.1 |
| ATCC 204660 | Saccharomyces cerevisiae | 8.7 | 0.0 | 9.3 | 26.8 |
| IFO 0339 | Saccharomycodes ludwigii | 15.3 | 0.0 | 6.0 | 80.9 |
| IAM 4842 | Schizosaccharomyces octosporus | 2.7 | 0.0 | 2.2 | 12.1 |
| IFO 1116 | Wickerhamia fluorescens | 18.7 | 0.0 | 4.2 | 23.0 |
| IFO 0794 | Debaryomyces hansenii var. fabryi | 4.8 | 2.7 | 7.7 | 11.5 |
| IFO 1359 | Debaryomyces castellii | 18.5 | 0.0 | 6.3 | 21.1 |

TABLE 2-continued

| Strain No. | Genus | Supernatant fraction (μg/L of culture solution) FOH | GGOH | Cell fraction (μg/L of culture solution) FOH | GGOH |
|---|---|---|---|---|---|
| JCM 2169 | *Debaryomyces vanrijiae var vanrijiae* | 73.7 | 0.0 | 14.3 | 6.2 |
| IFO 0115 | *Hanseniaspora valbyensis* | 13.6 | 0.0 | 7.4 | 103.5 |
| IFO 0118 | *Pichia anomala* | 0.0 | 0.0 | 2.2 | 15.3 |
| IFO 0569 | *Pichia anomala* | 0.0 | 0.0 | 7.3 | 28.2 |
| IFO 0941 | *Williopsis saturnus var. saturnus* | 4.7 | 0.0 | 69.8 | 78.7 |
| IFO 1475 | *Ogataea polymorpha* | 0.0 | 0.0 | 13.5 | 36.1 |
| IFO 1670 | *Pichia naganishii* | 1.2 | 2.1 | 0.0 | 0.0 |
| IFO 0707 | *Pichia anomala* | 8.6 | 0.6 | 0.0 | 12.3 |
| IFO 0719 | *Candida zeylanoides* | 10.2 | 0.0 | 4.4 | 20.3 |
| IFO 0701 | *Candida stellata* | 10.3 | 0.0 | 0.0 | 4.9 |
| IFO 0662 | *Kluyveromyces thermotolerans* | 13.7 | 0.0 | 10.4 | 9.2 |
| IFO 0648 | *Kluyveromyces lactis* | 16.0 | 0.0 | 6.3 | 72.9 |
| IFO 0005 | *Candida glabrata* | 35.7 | 5.4 | 4.5 | 28.3 |
| IFO 0595 | *Zygosaccharomyces japonicus* | 9.3 | 3.6 | 0.0 | 0.0 |

K: strain maintained by Kyoto University
FOH: farnesol
GGOH: geranylgeraniol

TABLE 3

| Strain No. | Genus | Supernatant fraction (μg/L of culture solution) FOH | GGOH | Cell fraction (μg/L of culture solution) FOH | GGOH |
|---|---|---|---|---|---|
| K 4003 | *Saccharomyces sp.* | 5.0 | 0.0 | 19.3 | 0.0 |
| K 4004 | *Saccharomyces sp.* | 10.6 | 0.0 | 15.2 | 0.0 |
| K 4011 | *Saccharomyces sake* | 0.0 | 0.0 | 9.0 | 0.0 |
| K 4021 | *Saccharomyces sake* | 0.0 | 0.0 | 2.2 | 0.0 |
| K 4101 | *Saccharomyces logos* | 0.0 | 0.0 | 18.4 | 0.0 |
| IFO 0686 | *Zygosaccharomyces rouxii* | 0.0 | 0.0 | 10.1 | 0.0 |
| IFO 0285 | *Saccharomyces dairensis* | 4.4 | 0.0 | 0.0 | 0.0 |
| IFO 0262 | *Saccharomyces cerevisiae* | 7.1 | 0.0 | 0.0 | 0.0 |
| IFO 0021 | *Zygosaccharomyces fermentati* | 5.4 | 0.0 | 0.0 | 0.0 |
| IFO 0259 | *Saccharomyces paradoxus* | 3.2 | 0.0 | 0.0 | 0.0 |
| IFO 0539 | *Saccharomyces bayanus* | 1.4 | 0.0 | 0.0 | 0.0 |
| IFO 0613 | *Saccharomyces bayanus* | 2.3 | 0.0 | 0.0 | 0.0 |
| IFO 0346 | *Schizosaccharomyces pombe* | 4.4 | 0.0 | 16.8 | 0.0 |
| IFO 0358 | *Schizosaccharomyces pombe* | 2.3 | 0.0 | 4.7 | 0.0 |
| IFO 0023 | *Debaryomyces hansenii* | 12.2 | 0.0 | 0.0 | 0.0 |
| IFO 0954 | *Citeromyces matritensis* | 8.5 | 0.0 | 0.0 | 0.0 |
| IFO 0974 | *Kuraishia capsulata* | 0.0 | 0.0 | 8.2 | 0.0 |
| IFO 0963 | *Pichia anomala* | 0.0 | 0.0 | 9.6 | 0.0 |
| IFO 0673 | *Waltomyces lipofer* | 10.1 | 0.0 | 0.0 | 0.0 |
| IFO 0678 | *Lypomyces starkeyi* | 4.8 | 0.0 | 0.0 | 0.0 |
| IFO 0579 | *Candida albicans* | 12.8 | 0.0 | 0.0 | 0.0 |
| IFO 0626 | *Candida utilis* | 3.0 | 0.0 | 0.0 | 0.0 |
| IFO 3022 | *Bacillus amyloliquefaciens* | 4.1 | 0.0 | 0.0 | 0.0 |
| IFO 3030 | *Bacillus pumilus* | 6.0 | 0.0 | 0.0 | 0.0 |
| IFO 3762 | *Staphylococcus epidermidis* | 6.1 | 0.0 | 0.0 | 0.0 |
| K 876 | *Pseudomonas sp.* | 18.6 | 0.0 | 0.0 | 0.0 |

K: strain maintained by Kyoto University
FOH: farnesol
GGOH: geranylgeraniol

TABLE 4

| Strain No. | Genus | Supernatant fraction (μg/L of culture solution) NE | FOH | GOH | Cell fraction (μg/L of culture solution) NE | FOH | GOH |
|---|---|---|---|---|---|---|---|
| IFO 12865 | *Streptomyces gardneri* | 0.0 | 0.0 | 0.0 | 11.5 | 0.0 | 0.0 |
| IFO 3384 | *Nocardia asteroides* | 0.0 | 0.0 | 0.0 | 14.2 | 0.0 | 0.0 |
| IFO 14340 | *Nocardia fusca* | 0.0 | 0.0 | 0.0 | 6.4 | 0.0 | 0.0 |

NE: nerolidol
FOH: farnesol
GGOH: geranylgeraniol

TABLE 5

| Strain No. | Medium composition | Cultivation period (days) | Supernatant fraction (μg/L of culture solution) Phosphatase-untreated FOH | GGOH | Phosphatase-treated FOH | GGOH |
|---|---|---|---|---|---|---|
| IFO 0005 | YM | 1 | 0.0 | 0.0 | 1.5 | 0.0 |
|  |  | 2 | 0.0 | 0.0 | 0.0 | 0.0 |
|  |  | 3 | 0.0 | 0.0 | 0.0 | 0.0 |
|  | YM + Glc | 1 | 0.0 | 0.0 | 6.1 | 0.0 |
|  |  | 2 | 0.0 | 0.0 | 9.5 | 0.0 |
|  |  | 3 | 29.4 | 2.3 | 13.9 | 0.0 |
|  | YM + Glc + SBO | 1 | 0.0 | 0.0 | 0.0 | 0.0 |
|  |  | 2 | 135.6 | 92.0 | 69.9 | 31.5 |
|  |  | 3 | 850.7 | 416.5 | 116.6 | 40.0 |
| IFO 0115 | YM | 1 | 0.0 | 0.0 | 0.0 | 0.0 |
|  |  | 2 | 0.0 | 0.0 | 0.0 | 0.0 |
|  |  | 3 | 34.0 | 0.0 | 0.0 | 0.0 |
|  | YM + Glc | 1 | 0.0 | 0.0 | 0.0 | 0.0 |
|  |  | 2 | 11.3 | 0.0 | 0.0 | 0.0 |
|  |  | 3 | 36.4 | 0.0 | 18.0 | 0.0 |
|  | YM + Glc + SBO | 1 | 0.0 | 0.0 | 0.0 | 0.0 |
|  |  | 2 | 24.0 | 0.0 | 5.1 | 0.0 |
|  |  | 3 | 30.3 | 26.5 | 7.9 | 0.0 |
| IFO 0339 | YM | 1 | 0.0 | 0.0 | 0.0 | 0.0 |
|  |  | 2 | 8.7 | 0.0 | 0.0 | 0.0 |
|  |  | 3 | 0.0 | 0.0 | 0.0 | 0.0 |
|  | YM + Glc | 1 | 0.0 | 0.0 | 0.0 | 0.0 |
|  |  | 2 | 16.8 | 0.0 | 17.7 | 0.0 |
|  |  | 3 | 67.1 | 0.0 | 20.8 | 0.0 |
|  | YM + Glc + SBO | 1 | 0.0 | 0.0 | 0.0 | 0.0 |
|  |  | 2 | 11.7 | 5.3 | 0.0 | 0.0 |
|  |  | 3 | 85.6 | 7.3 | 6.5 | 0.0 |

FOH: farnesol
GGOH: geranylgeraniol
YM: YM medium (Difco)
YM + Glc: YM medium (Difco) + 5% glucose
YM + Glc + SBO: YM medium (Difco) + 5% glucose + 1% soybean oil

TABLE 6

Medium composition: (see footnotes)

| Strain No. | Medium composition | Cultivation period (days) | Phosphatase-untreated FOH | Phosphatase-untreated GGOH | Phosphatase-treated FOH | Phosphatase-treated GGOH |
|---|---|---|---|---|---|---|
| IFO 0005 | YM | 1 | 39.4 | 0.0 | 0.0 | 0.0 |
| | | 2 | 14.8 | 37.3 | 0.0 | 0.0 |
| | | 3 | 11.4 | 41.7 | 51.2 | 0.0 |
| | YM + Glc | 1 | 8.4 | 0.0 | 0.0 | 0.0 |
| | | 2 | 44.1 | 134.4 | 86.8 | 304.8 |
| | | 3 | 104.4 | 323.9 | 202.4 | 772.6 |
| | YM + Glc + SBO | 1 | 5.8 | 0.0 | 0.0 | 0.0 |
| | | 2 | 427.4 | 178.9 | 248.0 | 239.6 |
| | | 3 | 835.3 | 363.7 | 1321.6 | 1176.2 |
| IFO 0115 | YM | 1 | 0.0 | 0.0 | 0.0 | 0.0 |
| | | 2 | 34.0 | 5.1 | 0.0 | 0.0 |
| | | 3 | 21.1 | 45.6 | 0.0 | 63.7 |
| | YM + Glc | 1 | 0.0 | 0.0 | 0.0 | 0.0 |
| | | 2 | 46.6 | 26.1 | 23.9 | 0.0 |
| | | 3 | 54.2 | 108.5 | 78.0 | 491.8 |
| | YM + Glc + SBO | 1 | 0.0 | 0.0 | 0.0 | 0.0 |
| | | 2 | 0.0 | 0.0 | 9.7 | 0.0 |
| | | 3 | 61.3 | 122.0 | 69.2 | 286.1 |
| IFO 0339 | YM | 1 | 18.0 | 0.0 | 0.0 | 0.0 |
| | | 2 | 16.6 | 0.0 | 0.0 | 0.0 |
| | | 3 | 19.5 | 48.3 | 0.0 | 71.0 |
| | YM + Glc | 1 | 0.0 | 0.0 | 0.0 | 0.0 |
| | | 2 | 58.6 | 34.1 | 12.0 | 0.0 |
| | | 3 | 62.3 | 173.8 | 67.8 | 464.8 |
| | YM + Glc + SBO | 1 | 0.0 | 0.0 | 0.0 | 0.0 |
| | | 2 | 96.4 | 10.3 | 9.3 | 0.0 |
| | | 3 | 61.6 | 103.7 | 27.9 | 135.6 |

FOH: farnesol
GGOH: geranylgeraniol
YM: YM medium (Difco)
YM + Glc: YM medium (Difco) + 5% glucose
YM + Glc + SBO: YM medium (Difco) + 5% glucose + 1% soybean oil

TABLE 7

Medium composition: YM medium (Difco)

| Strain No. | Genus | Supernatant fraction FOH | Supernatant fraction GGOH | Cell fraction FOH | Cell fraction GGOH |
|---|---|---|---|---|---|
| K 4104 | Saccharomyces cerevisiae | 0.0 | 0.0 | 15.8 | 31.7 |
| IFO 0252 | Saccharomyces rosei | 0.0 | 0.0 | 28.5 | 39.0 |
| IFO 0565 | Saccharomyces cerevisiae | 0.0 | 0.0 | 0.0 | 54.7 |
| IFO 0941 | Williopsis saturnus var. saturnus | 4.7 | 0.0 | 69.8 | 78.7 |
| IFO 1475 | Ogataea polymorpha | 0.0 | 0.0 | 13.5 | 36.1 |
| IFO 0648 | Kluyveromyces lactis | 6.0 | 0.0 | 6.3 | 72.9 |

K: strain maintained by Kyoto University
FOH: farnesol
GGOH: geranylgeraniol

TABLE 8

Medium composition: YM medium (Difco) + 5% glucose + 1% soybean oil

| Strain No. | Genus | Cultivation days | Supernatant fraction FOH | Supernatant fraction GGOH | Cell fraction FOH | Cell fraction GGOH |
|---|---|---|---|---|---|---|
| K 4104 | Saccharomyces cerevisiae | 3 | 281.0 | 127.7 | 241.1 | 161.6 |
| | | 6 | 338.2 | 186.9 | 155.3 | 132.2 |
| IFO 2052 | Saccharomyces rosei | 3 | 220.0 | 98.0 | 305.9 | 140.2 |
| | | 6 | 381.2 | 176.6 | 193.1 | 122.5 |
| IFO 0565 | Saccharomyces cerevisiae | 3 | 49.3 | 16.0 | 88.0 | 78.2 |
| | | 6 | 51.9 | 34.1 | 248.5 | 214.2 |
| IFO 0941 | Williopsis saturnus var. saturnus | 3 | 54.8 | 22.6 | 255.3 | 169.3 |
| | | 6 | 88.3 | 33.1 | 363.2 | 220.9 |
| IFO 1475 | Ogataea polymorpha | 3 | 60.9 | 69.1 | 113.5 | 127.2 |
| | | 6 | 19.8 | 14.6 | 60.8 | 95.9 |
| IFO 0648 | Kluyveromyces lactis | 3 | 28.5 | 37.8 | 61.8 | 91.1 |
| | | 6 | 120.3 | 124.5 | 159.8 | 211.5 |

K: strain maintained by Kyoto University
FOH: farnesol
GGOH: geranylgeraniol

TABLE 9

Medium composition: YM medium (Difco) + 4 mg/L ergosterol + 0–20 mg/L SQAD

| Strain No. | SQAD | Days | Supernatant NE | Supernatant FOH | Supernatant GGOH | Cell NE | Cell FOH | Cell GGOH |
|---|---|---|---|---|---|---|---|---|
| IFO 0215 Saccharomyces unisporus | 0 | 3 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 3.2 | 0.0 | 0.0 | 0.0 | 0.0 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 0538 Saccharomyces cerevisiae | 0 | 3 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 8.1 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 0622 Candida glabrata | 0 | 3 | 0.0 | 3.1 | 0.0 | 0.0 | 1.9 | 30.4 |
| | 1 | | 0.0 | 3.5 | 0.0 | 0.0 | 1.4 | 24.3 |
| | 20 | | 0.0 | 243.5 | 0.0 | 0.0 | 212.0 | 57.0 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 5.5 | 40.5 |
| IFO 0717 Yarrowia lopolytica | 0 | 3 | 0.0 | 0.0 | 0.0 | 0.0 | 0.0 | 0.0 |
| | 1 | | 0.0 | 1.3 | 0.0 | 0.0 | 0.0 | 0.0 |
| | 20 | | 0.0 | 39.7 | 66.5 | 0.0 | 39.7 | 63.5 |
| | 0 | 7 | 0.0 | 0.0 | 0.0 | 0.0 | 0.0 | 0.0 |
| | 1 | | 0.0 | 2.1 | 0.0 | 0.0 | 1.5 | 0.0 |
| | 20 | | 0.0 | 10.6 | 0.0 | 0.0 | 10.6 | 0.0 |
| IFO 0948 Komagataella | 0 | 3 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 3.4 | 2.3 | 0.0 | 3.4 | 1.8 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 0974 Kuraishia capsulata | 0 | 3 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 1472 Ogataea | 0 | 3 | 0.0 | 0.0 | 0.0 | 0.0 | 0.0 | 0.0 |
| | 1 | | 0.0 | 0.0 | 0.0 | 0.0 | 0.0 | 0.0 |

TABLE 9-continued

Medium composition: YM medium (Difco) + 4 mg/L ergosterol + 0–20 mg/L SQAD

| | | | Supernatant fraction | | | Cell fraction | | |
|---|---|---|---|---|---|---|---|---|
| | | | ($\mu$g/L of culture solution) | | | | | |
| Strain No. | SQAD | Days | NE | FOH | GGOH | NE | FOH | GGOH |
| glucozyma | 20 | | 0.0 | 0.0 | 18.3 | 0.0 | 0.0 | 17.5 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 6.8 |
| IFO 1892 | 0 | 3 | 0.0 | 0.0 | 0.0 | 0.0 | 0.0 | 8.9 |
| Saccharo- | 1 | | 0.0 | 0.0 | 0.0 | 0.0 | 0.0 | 16.7 |
| myces | 20 | | 0.0 | 0.0 | 0.0 | 0.0 | 0.0 | 38.5 |
| kluyeri | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 1910 | 0 | 3 | 0.0 | 0.0 | 0.0 | 0.0 | 0.0 | 0.0 |
| Candida | 1 | | 0.0 | 0.0 | 0.0 | 0.0 | 0.0 | 0.0 |
| cario- | 20 | | 0.0 | 0.0 | 0.0 | 0.0 | 0.0 | 5.5 |
| silignicola | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 0005 | 0 | 3 | 0.0 | 0.0 | 0.0 | 0.0 | 0.0 | 12.0 |
| Candia | 1 | | 0.0 | 0.0 | 0.0 | 0.0 | 0.0 | 4.3 |
| glabrata | 20 | | 0.0 | 33.8 | 2.7 | 0.0 | 0.0 | 53.7 |
| | 0 | 7 | 0.0 | 0.0 | 0.0 | 0.0 | 20.5 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |

I: strain purchased from IFO
NE: nerolidol
FOH: farnesol
GGOH: geranylgeraniol
SQAD: squalene synthesis inhibitor
0: none
1: 1 mg/L
20: 20 mg/L

TABLE 10

Medium composition: YM medium (Difco) + 5% glucose + 1% soybean oil + 4 mg/L ergosterol + 0–20 mg/L SQAD

| | | | Supernatant fraction | | | Cell fraction | | |
|---|---|---|---|---|---|---|---|---|
| | | | ($\mu$g/L of culture solution) | | | | | |
| Strain No. | SQAD | Days | NE | FOH | GGOH | NE | FOH | GGOH |
| IFO 0215 | 0 | 3 | 16.3 | 8.2 | 0.0 | 0.0 | 0.0 | 0.0 |
| Saccharomyces | 1 | | 12.2 | 5.2 | 0.0 | 0.0 | 0.0 | 0.0 |
| unisporus | 20 | | 67.4 | 68.4 | 0.0 | 0.0 | 16.9 | 0.0 |
| | 0 | 7 | 19.6 | 14.8 | 0.0 | 0.0 | 0.0 | 0.0 |
| | 1 | | 27.3 | 17.5 | 0.0 | 0.0 | 0.0 | 0.0 |
| | 20 | | 466.6 | 433.7 | 21.6 | 8.6 | 255.6 | 0.0 |
| IFO 0538 | 0 | 3 | 0.0 | 139.3 | 59.8 | 0.0 | 0.0 | 0.0 |
| Saccharomyces | 1 | | 0.0 | 102.9 | 46.2 | 0.0 | 15.5 | 0.0 |
| cerevisiae | 20 | | 65.9 | 9087.5 | 331.6 | 0.0 | 1465.9 | 51.0 |
| | 0 | 7 | 0.0 | 426.4 | 246.7 | 0.0 | 38.0 | 0.0 |
| | 1 | | 0.0 | 319.5 | 241.0 | 0.0 | 188.8 | 85.6 |
| | 20 | | 216.2 | 34241.4 | 1568.8 | 18.4 | 5812.1 | 266.2 |
| IFO 0622 | 0 | 3 | 0.0 | 106.1 | 112.3 | 0.0 | 28.8 | 33.6 |
| Candida | 1 | | 9.4 | 149.2 | 119.7 | 0.0 | 9.7 | 0.0 |
| glabrata | 20 | | 422.2 | 12186.9 | 327.2 | 0.0 | 331.6 | 9.3 |
| | 0 | 7 | 11.6 | 378.3 | 408.5 | 0.0 | 43.7 | 59.2 |
| | 1 | | 17.2 | 530.0 | 231.5 | 0.0 | 133.3 | 58.5 |
| | 20 | | 1256.9 | 22147.1 | 862.7 | 138.0 | 2750.6 | 170.5 |
| IFO 0717 | 0 | 3 | 0.0 | 8.7 | 0.0 | 0.0 | 6.7 | 0.0 |
| Yarrowia | 1 | | 2.4 | 100.1 | 19.1 | 0.0 | 165.3 | 0.0 |
| lopolytica | 20 | | 19.0 | 983.3 | 17.8 | 0.0 | 882.1 | 0.0 |
| | 0 | 7 | 0.0 | 95.3 | 608.0 | 0.0 | 0.0 | 38.4 |
| | 1 | | 19.0 | 405.4 | 546.8 | 0.0 | 0.0 | 0.0 |
| | 20 | | 156.7 | 6812.9 | 76.2 | 0.0 | 1025.1 | 41.8 |
| IFO 0948 | 0 | 3 | 0.0 | 73.5 | 78.9 | 0.0 | 13.8 | 42.3 |
| Komagataella | 1 | | 0.0 | 82.2 | 71.5 | 0.0 | 22.9 | 28.4 |
| pastoris | 20 | | 17.2 | 2956.2 | 132.5 | 0.0 | 608.4 | 80.1 |
| | 0 | 7 | 0.0 | 101.6 | 83.5 | 0.0 | 4.3 | 11.0 |
| | 1 | | 0.0 | 569.8 | 235.7 | 0.0 | 53.4 | 28.2 |
| | 20 | | 34.2 | 5513.3 | 360.4 | 0.0 | 537.5 | 84.5 |
| IFO 0974 | 0 | 3 | 0.0 | 24.8 | 11.1 | 0.0 | 3.3 | 0.0 |
| Kuraishia | 1 | | 0.0 | 1061.9 | 46.1 | 0.0 | 16.1 | 7.5 |
| capsulata | 20 | | 0.0 | 2022.7 | 262.0 | 0.0 | 149.2 | 34.8 |
| | 0 | 7 | 0.0 | 167.5 | 236.3 | 0.0 | 3.2 | 8.5 |

TABLE 10-continued

Medium composition: YM medium (Difco) + 5% glucose + 1% soybean oil + 4 mg/L ergosterol + 0–20 mg/L SQAD

| | | | Supernatant fraction | | | Cell fraction | | |
|---|---|---|---|---|---|---|---|---|
| | | | (μg/L of culture solution) | | | | | |
| Strain No. | SQAD | Days | NE | FOH | GGOH | NE | FOH | GGOH |
| | 1 | | 0.0 | 713.7 | 275.7 | 0.0 | 24.8 | 21.2 |
| | 20 | | 35.9 | 8268.5 | 680.4 | 0.0 | 362.1 | 59.7 |
| IFO 1472 | 0 | 3 | 0.0 | 34.8 | 79.8 | 0.0 | 7.4 | 20.4 |
| Ogataea | 1 | | 0.0 | 40.5 | 86.0 | 0.0 | 3.7 | 9.5 |
| glucozyma | 20 | | 0.0 | 808.8 | 278.7 | 0.0 | 41.1 | 37.5 |
| | 0 | 7 | 0.0 | 63.2 | 138.8 | 0.0 | 0.0 | 0.0 |
| | 1 | | 0.0 | 93.8 | 114.7 | 0.0 | 0.0 | 0.0 |
| | 20 | | 0.0 | 1832.0 | 513.0 | 0.0 | 73.7 | 52.6 |
| IFO 1892 | 0 | 3 | 0.0 | 70.4 | 46.1 | 0.0 | 3.7 | 0.0 |
| Saccharomyces | 1 | | 0.0 | 51.4 | 23.0 | 0.0 | 2.3 | 0.0 |
| kluyeri | 20 | | 0.0 | 62.9 | 30.7 | 0.0 | 16.5 | 0.0 |
| | 0 | 7 | 0.0 | 158.5 | 71.4 | 0.0 | 0.0 | 0.0 |
| | 1 | | 23.5 | 188.3 | 101.7 | 0.0 | 5.0 | 0.0 |
| | 20 | | 44.1 | 935.3 | 126.4 | 0.0 | 227.8 | 27.8 |
| IFO 1910 | 0 | 3 | 0.0 | 11.0 | 44.7 | 0.0 | 0.0 | 0.0 |
| Candida | 1 | | 0.0 | 20.9 | 69.3 | 0.0 | 0.0 | 0.0 |
| cariosilignicola | 20 | | 0.0 | 124.9 | 127.1 | 0.0 | 8.1 | 19.6 |
| | 0 | 7 | 0.0 | 51.7 | 152.9 | 0.0 | 0.0 | 0.0 |
| | 1 | | 0.0 | 257.7 | 367.3 | 0.0 | 10.3 | 37.4 |
| | 20 | | 0.0 | 14378.1 | 2997.2 | 0.0 | 845.5 | 205.0 |
| IFO 0005 | 0 | 3 | 22.9 | 552.1 | 496.1 | 0.0 | 50.5 | 75.2 |
| Candia | 1 | | 260.0 | 6784.9 | 818.5 | 8.6 | 462.0 | 86.5 |
| glabrata | 20 | | 2384.0 | 37513.9 | 1022.9 | 423.9 | 9405.0 | 306.5 |
| | 0 | 7 | 77.1 | 1676.1 | 1434.6 | 0.0 | 41.2 | 51.2 |
| | 1 | | 546.0 | 11219.5 | 1377.8 | 9.2 | 331.7 | 77.1 |
| | 20 | | 6208.9 | 68495.6 | 3228.1 | 139.2 | 2682.5 | 217.6 |

NE: nerolidol
FOH: farnesol
GGOH: geranylgeraniol
SQAD: squalene synthesis inhibitor
0: none
1: 1 mg/L
20: 20 mg/L

TABLE 11

Medium composition: YM or KB or KY medium + 1% soybean oil + 6% glucose + 4 mg/L ergosterol

| | | | Supernatant fraction (μg/L) | | |
|---|---|---|---|---|---|
| Medium | Strain No. | SQAD | NE | FOH | GGOH |
| YM | IFO 0107 | 0 | 0.0 | 10.8 | 155.2 |
| | Saccharomycopsis fibuligera | 20 | 0.0 | 9.7 | 386.5 |
| KB | K 0876 | 0 | 0.0 | 29.0 | 0.0 |
| | Pseudomonas sp | 20 | 0.0 | 7.8 | 0.0 |
| YM | IFO 1665 | 0 | 0.0 | 4.7 | 211.5 |
| | Saccharomycopsis fibuligera | 20 | 0.0 | 94.5 | 4214.9 |
| YM | IFO 1744 | 0 | 0.0 | 0.0 | 155.5 |
| | Saccharomycopsis fibuligera | 20 | 0.0 | 41.1 | 3870.1 |
| KB | K 2103 | 0 | 0.0 | 10.9 | 0.0 |
| | Norcadia asteroides | 20 | 0.0 | 0.0 | 0.0 |
| KY | IFO 4570 | 0 | 0.0 | 0.0 | 36.5 |
| | Mucor Javanicus | 20 | 0.0 | 38.8 | 343.6 |
| KY | K 4003 | 0 | 30.1 | 511.9 | 694.7 |
| | Saccharomyces Hafe logos van Laer | 20 | 4980.0 | 56541.1 | 3603.4 |
| KY | K 4045 | 0 | 148.1 | 870.4 | 766.8 |
| | Saccharomyces cerevisiae | 20 | 24606.3 | 37772.7 | 2590.6 |
| KY | K 4102 | 0 | 17.5 | 541.1 | 711.3 |
| | Saccharomyces ellipsoideus | 20 | 18160.8 | 50245.8 | 3207.1 |
| KY | K 4103 | 0 | 56.4 | 753.1 | 1072.8 |
| | Saccharomyces cerevisiae | 20 | 20930.8 | 53814.6 | 4589.9 |
| KY | K 4104 | 0 | 19.5 | 569.2 | 546.0 |
| | Saccharomyces cerevisiae | 20 | 23620.7 | 54713.2 | 2654.4 |
| KY | IFO 0565 | 0 | 0.0 | 411.7 | 535.2 |
| | Saccharomyces cerevisiae | 20 | 839.9 | 45723.6 | 2216.6 |
| KY | IFO 0210 | 0 | 37.5 | 685.5 | 362.8 |
| | Saccharomyces cerevisiae | 20 | 25251.0 | 48795.6 | 1627.2 |
| KY | IFO 0346 | 0 | 0.0 | 196.2 | 278.9 |
| | Schizosaccharomyces pombe | 20 | 757.6 | 45282.1 | 1153.6 |
| KY | IFO 1475 | 0 | 0.0 | 236.9 | 462.7 |
| | Ogataea polymorpha | 20 | 0.0 | 5643.0 | 1195.1 |
| KY | JCM 2169 | 0 | 0.0 | 809.6 | 241.2 |
| | Debaryomyces vanrijiae var vanrijiae | 20 | 129.5 | 20359.5 | 2236.0 |
| KY | IFO 0339 | 0 | 0.0 | 164.4 | 864.3 |
| | Saccharomycodes ludwigii | 20 | 131.0 | 28498.6 | 1483.8 |

TABLE 11-continued

Medium composition: YM or KB or KY medium + 1% soybean oil + 6% glucose + 4 mg/L ergosterol

| Medium | Strain No. | Supernatant fraction ($\mu$g/L) | | | |
|---|---|---|---|---|---|
| | | SQAD | NE | FOH | GGOH |
| KY | IFO 0115 | 0 | 0.0 | 254.9 | 493.6 |
| | Hanseniaspora valbyensis Valbyensis | 20 | 182.6 | 26807.1 | 1217.7 |
| KY | IFO 0648 | 0 | 0.0 | 136.4 | 433.8 |
| | Kluyveromyces lactis | 20 | 348.6 | 31785.7 | 3343.8 |
| KY | IFO 0005 | 0 | 192.8 | 861.5 | 909.0 |
| | Candida glabrata | 20 | 15504.1 | 44573.8 | 2237.1 |
| KY | IFO 0762 | 0 | 37.0 | 274.7 | 384.4 |
| | Candida solani | 20 | 1702.8 | 6574.7 | 619.1 |
| KY | IFO 1527 | 0 | 0.0 | 16.6 | 24.7 |
| | Cryptococcus humicolus | 20 | 0.0 | 49.6 | 33.4 |
| KY | IFO 1116 | 0 | 0.0 | 199.3 | 315.7 |
| | Wickerhamia fluorescens | 20 | 73.2 | 12200.1 | 1181.6 |

NE: nerolidol
FOH: farnesol
GGOH: geranylgeraniol
SQAD: squalene synthesis inhibitor   0: none   20: 20 mg/L
Treated with phosphatase

TABLE 12

Medium composition: YM or KB or KY medium + 1% soybean oil + 6% glucose + 4 mg/L ergosterol

| Medium | Strain No. | Cell fraction ($\mu$g/L) | | | |
|---|---|---|---|---|---|
| | | SQAD | NE | FOH | GGOH |
| YM | IFO 0107 | 0 | 0.0 | 8.1 | 24.6 |
| | Saccharomycopsis fibuligera | 20 | 0.0 | 4.8 | 79.9 |
| KB | K 0876 | 0 | 0.0 | 0.0 | 0.0 |
| | Pseudomonas sp. H21 | 20 | 0.0 | 0.0 | 0.0 |
| YM | IFO 1665 | 0 | 0.0 | 8.2 | 21.7 |
| | Saccharomycopsis fibuligera | 20 | 0.0 | 20.8 | 228.9 |
| YM | IFO 1744 | 0 | 0.0 | 0.0 | 42.2 |
| | Saccharomycopsis fibuligera | 0 | 0.0 | 29.8 | 819.1 |
| KB | K 2103 | 0 | | | |
| | Norcadia asteroides | 20 | | | |
| KY | IFO 4570 | 0 | 13.4 | 22.7 | 17.5 |
| | Mucor Javanicus | 20 | 0.0 | 15.6 | 61.7 |
| KY | K 4003 | 0 | 0.0 | 36.9 | 52.4 |
| | Saccharomyces Hafe logos van Laer | 20 | 291.8 | 7433.0 | 710.6 |
| KY | K 4045 | 0 | 0.0 | 69.3 | 65.8 |
| | Saccharomyces cerevisiae | 20 | 3022.6 | 7893.0 | 534.5 |
| KY | K 4102 | 0 | 0.0 | 36.4 | 76.3 |
| | Saccharomyces ellipsoideus | 20 | 1350.0 | 6358.2 | 396.5 |
| KY | K 4103 | 0 | 0.0 | 591.7 | 39.4 |
| | Saccharomyces cerevisiae | 20 | 1073.6 | 5528.9 | 369.6 |
| KY | K 4104 | 0 | 0.0 | 51.6 | 79.2 |
| | Saccharomyces cerevisiae | 20 | 2409.9 | 11464.9 | 656.2 |
| KY | IFO 0565 | 0 | 0.0 | 40.2 | 54.7 |
| | Saccharomyces cerevisiae | 20 | 57.3 | 5071.6 | 333.5 |
| KY | IFO 0210 | 0 | 0.0 | 119.4 | 89.6 |
| | Saccharomyces cerevisiae | 20 | 1698.7 | 4355.2 | 83.2 |
| KY | IFO 0346 | 0 | 0.0 | 29.7 | 82.6 |
| | Schizosaccharomyces pombe | 20 | 83.1 | 4826.5 | 159.4 |

TABLE 12-continued

Medium composition: YM or KB or KY medium + 1% soybean oil + 6% glucose + 4 mg/L ergosterol

| Medium | Strain No. | Cell fraction ($\mu$g/L) | | | |
|---|---|---|---|---|---|
| | | SQAD | NE | FOH | GGOH |
| KY | IFO 1475 | 0 | 0.0 | 31.4 | 126.0 |
| | Ogataea polymorpha | 20 | 19.8 | 1196.1 | 402.7 |
| KY | JCM 2169 | 0 | 0.0 | 67.2 | 54.3 |
| | Debaryomyces vanrijiae var vanrijiae | 20 | 23.9 | 2807.0 | 492.6 |
| KY | IFO 0339 | 0 | 0.0 | 41.6 | 114.7 |
| | Saccharomycodes ludwigii | 20 | 0.0 | 3217.2 | 199.4 |
| KY | IFO 0115 | 0 | 0.0 | 25.2 | 76.6 |
| | Hanseniaspora valbyensis Valbyensis | 20 | 15.1 | 2823.5 | 185.8 |
| KY | IFO 0648 | 0 | 0.0 | 20.9 | 84.6 |
| | Kluyveromyces lactis | 20 | 14.5 | 1128.6 | 225.8 |
| KY | IFO 0005 | 0 | 0.0 | 34.9 | 51.7 |
| | Candida glabrata | 20 | 1193.0 | 4710.9 | 279.6 |
| KY | IFO 0762 | 0 | 16.2 | 90.5 | 126.0 |
| | Candida solani | 20 | 231.3 | 962.5 | 350.0 |
| KY | IFO 1527 | 0 | 7.8 | 16.0 | 0.0 |
| | Cryptococcus humicolus | 20 | 21.2 | 160.9 | 51.9 |
| KY | IFO 1116 | 0 | 0.0 | 15.0 | 86.5 |
| | Wickerhamia fluorescens | 20 | 32.6 | 4262.8 | 500.7 |

NE: nerolidol
FOH: farnesol
GGOH: geranylgeraniol
SQAD: squalene synthesis inhibitor   0: none   20: 20 mg/L
Treated with phosphatase

TABLE 13

Medium composition: KB medium + 1% soybean oil + ergosterol

| Strain No. | SQAD | Supernatant fraction ($\mu$g/L of culture solution) | | | Cell fraction | | |
|---|---|---|---|---|---|---|---|
| | | NE | FOH | GGOH | NE | FOH | GGOH |
| IFO 3032 | 0 | 0.0 | 11.6 | 0.0 | 0.0 | 0.0 | 0.0 |
| Baccilus Amyloliquefaciens | 20 | 0.0 | 22.4 | 0.0 | 0.0 | 0.0 | 0.0 |
| IFO 3030 | 0 | 0.0 | 21.9 | 0.0 | 0.0 | 0.0 | 0.0 |
| Baccilus pumilus | 20 | 0.0 | 36.6 | 0.0 | 0.0 | 6.0 | |
| IFO 3762 | 0 | 0.0 | 6.8 | 0.0 | 0.0 | 11.2 | 0.0 |
| Staphylococcus Epidermidis | 20 | 0.0 | 121.4 | 0.0 | 0.0 | 292.4 | 0.0 |
| IFO 3067 | 0 | 0.0 | 5.1 | 0.0 | 0.0 | 0.0 | 0.0 |
| Micrococcus Lutenus | 20 | 0.0 | 57.3 | 0.0 | 0.0 | 11.8 | 0.0 |
| IFO 12146 | 0 | 0.0 | 0.0 | 0.0 | 0.0 | 0.0 | 0.0 |
| Exiguobacterium Acetylicum | 20 | 0.0 | 115.7 | 0.0 | 0.0 | 10.4 | 0.0 |

NE: nerolidol
FOH: farnesol
GGOH: geranylgeraniol
SQAD: squalene synthesis inhibitor   0: none   20: 20 mg/L
Treated with phosphatase

TABLE 14

Production of nerolidol (NOH), farnesol (FOH) and geranylgeraniol (GGOH) (mg/L of culture solution)

| | | Day 3 | | | Day 10 | | | | |
|---|---|---|---|---|---|---|---|---|---|
| Strains | No. | NOH | FOH | GGOH | NOH | FOH | GGOH | Temp. | Medium |
| *Alcaligenes faecalis* | IFO 13111 | 0.00 | 0.01 | 0.11 | 0.00 | 0.04 | 0.09 | 30 | LBO-SSI |
| *Brevibacterium divaricatum* | NRRL 2311 | 0.00 | 0.00 | 0.02 | 0.00 | 0.00 | 0.00 | 30 | LBO-SSI |
| *Brevibacterium fuscum* | IFO 12127 | 0.00 | 0.02 | 0.00 | 0.00 | 0.00 | 0.00 | 30 | LBO-SSI |
| *Brevibacterium linens* | IFO 12171 | 0.00 | 0.46 | 0.00 | 0.00 | 0.08 | 0.00 | 30 | LBO-SSI |
| *Candida catenulata* | IFO 0720 | 0.04 | 8.10 | 0.34 | 0.04 | 8.61 | 0.47 | 30 | YMO-SSI |
| *Candida fragicola* | IFO 1574 | 0.03 | 4.91 | 0.76 | 0.04 | 8.95 | 1.31 | 30 | YMO-SSI |
| *Candida krusei* | IFO 0013 | 0.04 | 6.99 | 0.29 | 0.06 | 13.65 | 0.86 | 30 | YMO-SSI |
| *Candida lambica* | IFO 1146 | 0.02 | 4.53 | 0.49 | 0.04 | 0.59 | 1.24 | 30 | YMO-SSI |
| *Candida maltosa* | IFO 1977 | 0.00 | 6.74 | 0.19 | 0.08 | 9.03 | 0.58 | 30 | YMO-SSI |
| *Candida mycoderma* | IFO 0164 | 0.02 | 5.45 | 0.20 | 0.03 | 4.69 | 0.17 | 30 | YMO-SSI |
| *Candida parapsilosis* | IFO 0708 | 0.00 | 1.76 | 0.17 | 0.01 | 5.13 | 0.25 | 30 | YMO-SSI |
| *Candida rugosa* | IFO 0591 | 0.00 | 0.90 | 0.08 | 0.00 | 4.20 | 0.19 | 30 | YMO-SSI |
| *Candida succiphila* | IFO 1911 | 0.00 | 2.44 | 0.25 | 0.00 | 0.00 | 0.00 | 30 | YMO-SSI |
| *Candida tropicalis* | IFO 0006 | | ><><>< | | 0.17 | 9.04 | 0.00 | 30 | YMO-SSI |
| *Candida zeylanoides* | IFO 0719 | 0.00 | 1.43 | 0.29 | 0.00 | 7.38 | 1.24 | 30 | YMO-SSI |
| *Cryptococcus albidus* | IFO 0881 | 0.00 | 0.15 | 0.03 | 0.02 | 2.41 | 0.45 | 30 | YMO-SSI |
| *Cryptococcus glutinis* | IFO 1125 | 0.04 | 6.64 | 1.48 | 0.35 | 3.70 | 3.29 | 24 | YMO-SSI |
| *Dipodascus ovetensis* | IFO 1201 | 0.00 | 4.23 | 0.14 | 0.04 | 8.68 | 0.95 | 30 | YMO-SSI |
| *Haloferax volcanii* | IFO 14742 | 2.12 | 39.11 | 1.04 | 4.14 | 57.73 | 2.49 | 30 | HVO-SSI |
| *Hanseniaspora valbyensis* | IFO 1758 | 0.00 | 0.33 | 0.04 | 0.04 | 2.40 | 0.12 | 30 | YMO-SSI |
| *Issatchenkia orientalis* | IFO 1279 | 0.00 | 2.22 | 0.15 | 0.03 | 7.68 | 0.52 | 30 | YMO-SSI |
| *Kloeckera africana* | IFO 0868 | 1.09 | 10.90 | 0.81 | 1.10 | 6.29 | 0.17 | 30 | YMO-SSI |
| *Kloeckera apiculata* | IFO 0151 | 0.00 | 0.05 | 0.02 | 1.04 | 10.73 | 0.86 | 30 | YMO-SSI |
| *Kluyveromyces marxianus* | IFO 0617 | 0.09 | 14.48 | 0.87 | 0.13 | 16.29 | 1.71 | 30 | YMO-SSI |
| *Kuraishia capsulata* | IFO 0974 | 0.00 | 0.91 | 0.17 | 0.00 | 3.25 | 0.42 | 30 | YMO-SSI |
| *Mortierella ramanniana* | ATCC 24786 | | ><><>< | | 0.00 | 0.76 | 0.13 | 24 | YMO-SSI |
| *Nakazawaea holstii* | IFO 0980 | 0.01 | 1.06 | 0.18 | 0.02 | 5.85 | 0.38 | 30 | YMO-SSI |
| *Pichia capsulata* | IFO 0984 | 0.00 | 0.63 | 0.04 | 0.04 | 4.17 | 0.11 | 30 | YMO-SSI |
| *Pichia henricii* | IFO 1477 | 0.00 | 3.20 | 0.12 | 0.00 | 3.24 | 0.00 | 30 | YMO-SSI |
| *Pichia holstii* | IFO 0980 | 0.04 | 6.22 | 0.22 | 0.04 | 2.79 | 0.65 | 30 | YMO-SSI |
| *Pichia naganishii* | IFO 1670 | 0.00 | 2.14 | 0.12 | 0.02 | 9.28 | 0.96 | 30 | YMO-SSI |
| *Pichia rhodanensis* | IFO 1272 | 0.03 | 3.34 | 0.91 | 0.46 | 26.57 | 10.29 | 30 | YMO-SSI |
| *Pichia saitoi* | IAM 4945 | 0.34 | 10.78 | 0.51 | 0.28 | 24.31 | 1.38 | 30 | YMO-SSI |
| *Rhodosporidium toruloides* | IFO 8766 | 0.88 | 6.59 | 2.47 | 0.72 | 2.47 | 2.52 | 24 | YMO-SSI |
| *Rhodotorula aurantinaca* | IFO 0951 | 0.01 | 3.14 | 0.15 | 0.03 | 6.11 | 0.50 | 30 | YMO-SSI |
| *Rhodotorula rubra* | IFO 0870 | 0.03 | 1.62 | 1.02 | 0.16 | 2.32 | 1.61 | 30 | YMO-SSI |
| *Saccharomycopsis fibuligera* | IFO 0105 | 0.00 | 0.06 | 1.68 | 0.00 | 5.71 | 4.79 | 30 | YMO-SSI |
| *Saccharomycopsis lipolytica* | IFO 1209 | 0.05 | 9.48 | 0.16 | 0.21 | 16.46 | 0.83 | 30 | YMO-SSI |
| *Schizosaccharomyces octosporus* | IAM 4842 | 0.00 | 1.24 | 0.03 | 0.00 | 1.79 | 0.08 | 30 | YMO-SSI |
| *Staphylococcus aureus* | IFO 3060 | 0.00 | 0.06 | 0.00 | 0.00 | 0.05 | 0.00 | 30 | YMO-SSI |
| *Torulaspora delbrueckii* | IFO 1626 | 0.04 | 2.33 | 0.15 | 0.06 | 5.50 | 0.36 | 30 | YMO-SSI |
| *Trichosporon cutaneum* | IFO 1198 | 0.00 | 10.23 | 0.69 | 0.00 | 0.14 | 0.09 | 30 | YMO-SSI |
| *Tsukamurella paurometabolum* | IFO 12160 | 0.00 | 0.07 | 0.00 | 0.00 | 0.06 | 0.00 | 30 | YMO-SSI |
| *Yamadazyma farinosa* | IFO 0193 | 0.00 | 1.27 | 0.18 | 0.00 | 2.36 | 0.82 | 30 | YMO-SSI |
| *Yerroiwa lipolytica* | IFO 0746 | 0.06 | 9.66 | 0.15 | 0.16 | 13.41 | 0.36 | 24 | YMO-SSI |
| *Zygosaccharomyces japonicus* | IFO 0595 | 0.05 | 0.77 | 0.05 | 0.10 | 2.17 | 0.15 | 30 | YMO-SSI |

| | | Day 3 | | | Day 10 | | | Temp. | |
|---|---|---|---|---|---|---|---|---|---|
| Strains | IFO No. | NOH | FOH | GGOH | NOH | FOH | GGOH | (° C.) | Medium |
| *Ambrosiozyma ambrosiae* | 10835 | 0.0 | 0.1 | 1.5 | 0.0 | 0.0 | 0.7 | 24 | YPDO-SSI |
| *Ambrosiozyma monospora* | 10751 | 0.0 | 1.0 | 0.3 | 0.0 | 4.8 | 1.4 | 24 | YMO-SSI |
| *Ambrosiozyma philentoma* | 1847 | 0.0 | 0.9 | 0.2 | 0.0 | 16.8 | 0.8 | 24 | YMO-SSI |
| *Ambrosiozyma platypodis* | 10752 | 0.0 | 1.7 | 0.1 | 0.0 | 48.6 | 1.4 | 24 | YMO-SSI |
| *Bensingtonia intermedia* | 10178 | 0.0 | 1.5 | 0.7 | 0.0 | 2.9 | 5.2 | 24 | YMO-SSI |
| *Botryozyma nematodophila* | 10830 | 0.0 | 2.5 | 0.3 | 0.0 | 5.6 | 2.8 | 24 | YPOO-SSI |
| *Brettanomyces anomalus* | 0627 | 0.0 | 18.0 | 0.4 | 0.6 | 16.7 | 0.0 | 24 | YMO-SSI |
| *Brettanomyces bruxellensis* | 0797 | 0.0 | 4.7 | 0.5 | 0.0 | 8.2 | 0.0 | 24 | YMO-SSI |
| *Brettanomyces custersianus* | 10735 | 0.0 | 0.1 | 1.4 | 0.0 | 20.0 | 0.6 | 24 | YMO-SSI |
| *Bullera crocea* | 10113 | 0.0 | 7.4 | 0.5 | 0.0 | 16.1 | 0.5 | 17 | YMO-SSI |
| *Bullera sinensis* | 10756 | 0.1 | 0.3 | 1.0 | 0.1 | 1.7 | 2.3 | 24 | YMO-SSI |
| *Citeromyces matritensis* | 0651 | 0.1 | 2.0 | 0.4 | 0.0 | 0.7 | 0.0 | 24 | YMO-SSI |
| *Clavispora lusitaniae* | 10059 | 0.0 | 1.0 | 0.3 | 0.1 | 9.2 | 9.1 | 24 | YMO-SSI |
| *Cystofilobasidium infirmominiatum* | 1057 | 5.7 | 14.9 | 2.6 | 10.8 | 48.4 | 3.6 | 24 | YMO-SSI |
| *Debaryomyces occidentalis* | 1842 | 0.0 | 0.7 | 0.2 | 0.0 | 0.4 | 4.1 | 24 | YMO-SSI |
| *Dekkera bruxellensis* | 1590 | 0.0 | 3.7 | 0.2 | 0.0 | 15.7 | 0.0 | 24 | YMO-SSI |
| *Dipodascus armillariae* | 10804 | 0.0 | 4.2 | 0.1 | 0.0 | 3.3 | 0.2 | 24 | YMO-SSI |
| *Dipodascus tetrasperma* | 10810 | 0.0 | 1.7 | 0.8 | 0.0 | 9.8 | 2.5 | 24 | YMO-SSI |
| *Eremascus albus* | 10811 | 0.0 | 0.0 | 4.8 | 0.0 | 0.0 | 3.6 | 24 | YMO-SSI |
| *Eremascus fertilis* | 0691 | 0.0 | 0.0 | 0.0 | 0.0 | 0.4 | 0.0 | 24 | YMO-SSI |
| *Eremothecium gossypii* | 1355 | 0.0 | 0.8 | 0.0 | 0.0 | 4.4 | 0.9 | 24 | YMO-SSI |
| *Erythrobasidium hasegawianum* | 1058 | 0.0 | 0.5 | 1.0 | 0.0 | 0.0 | 6.8 | 24 | YMO-SSI |

TABLE 14-continued

Production of nerolidol (NOH), farnesol (FOH) and geranylgeraniol (GGOH) (mg/L of culture solution)

| Strains | No. | NOH | FOH | GGOH | NOH | FOH | GGOH | Temp. (° C.) | Medium |
|---|---|---|---|---|---|---|---|---|---|
| Hanseniaspora guilliermondii | 1411 | 0.0 | 1.4 | 0.1 | 0.0 | 1.3 | 0.0 | 24 | YMO-SSI |
| Hanseniaspora uvarum | 10833 | 0.1 | 15.3 | 2.9 | 0.4 | 11.1 | 0.8 | 24 | YPDO-SSI |
| Kloeckeraspora vineae | 1415 | 0.4 | 3.4 | 0.3 | 0.7 | 1.2 | 0.0 | 24 | YMO-SSI |
| Kockovaella imperatae | 10522 | 0.0 | 3.2 | 3.5 | 0.0 | 19.5 | 6.2 | 24 | YMO-SSI |
| Kodamaea ohmeri | 0202 | 0.0 | 7.7 | 1.6 | 0.1 | 13.7 | 4.7 | 24 | YMO-SSI |
| Kurtzmanomyces nectairei | 10118 | 0.0 | 0.1 | 0.1 | 0.0 | 0.0 | 0.0 | 24 | YMO-SSI |
| Leucosporidium scottii | 1924 | 0.2 | 32.8 | 1.3 | 0.7 | 5.2 | 0.0 | 24 | YMO-SSI |
| Lodderomyces elongisporus | 1676 | 0.1 | 14.8 | 2.0 | 0.1 | 15.7 | 0.0 | 24 | YMO-SSI |
| Malassezia furfur | 0656 | 0.0 | 4.3 | 0.1 | 0.0 | 6.9 | 0.1 | 30 | YMDO-SSI |
| Metschnikowia hawaiiensis | 10791 | 0.0 | 0.0 | 0.3 | 0.0 | 0.0 | 0.2 | 24 | YPDO-SSI |
| Metschnikowia krissii | 1677 | 0.0 | 1.3 | 0.1 | 0.0 | 21.0 | 0.0 | 24 | YMO-SSI |
| Metschnikowia lunata | 1605 | 0.0 | 5.1 | 1.0 | 0.3 | 31.9 | 5.9 | 24 | YMO-SSI |
| Metschnikowia pulcherrima | 0863 | 0.0 | 10.5 | 0.2 | 0.1 | 15.4 | 0.3 | 24 | YMO-SSI |
| Mrakia frigida | 1926 | 0.5 | 25.3 | 0.3 | 0.3 | 11.3 | 0.1 | 12 | YMO-SSI |
| Myxazyma lipomycoides | 10351 | 0.7 | 23.3 | 5.4 | 1.3 | 35 | 1.1 | 24 | YMO-SSI |
| Nadsonia commutata | 10029 | 0.0 | 0.1 | 0.0 | 0.0 | 0.3 | 0.0 | 17 | YMO-SSI |
| Pachysolen tannophilus | 1007 | 0.0 | 0.1 | 0.1 | 0.0 | 1.9 | 1.4 | 24 | YMO-SSI |
| Pichia burtonii | 10837 | 0.0 | 3.0 | 1.1 | 0.0 | 7.5 | 1.7 | 24 | YMO-SSI |
| Pichia misumaiensis | 10221 | 0.3 | 20.8 | 1.8 | 1.0 | 14.5 | 2.0 | 24 | YMO-SSI |
| Pichia ofunaensis | 10709 | 0.0 | 0.1 | 0.1 | 0.0 | 0.0 | 0.0 | 24 | YMO-SSI |
| Pichia pijperi | 1290 | 0.5 | 5.1 | 0.6 | 0.5 | 6.4 | 0.5 | 24 | YMO-SSI |
| Saccharomyces transvaalensis | 1625 | 0.1 | 0.0 | 0.0 | 0.0 | 0.0 | 0.0 | 30 | YMO-SSI |
| Sacoharomycodes sinensis | 10111 | 0.1 | 0.4 | 0.0 | 0.6 | 0.8 | 0.1 | 30 | YMO-SSI |
| Saccharomycopsis fibuligera | 10829 | 0.0 | 0.0 | 4.1 | 0.0 | 0.0 | 2.8 | 24 | YPDO-SSI |
| Saccharomycopsis javaensis | 1848 | 0.0 | 0.0 | 0.0 | 0.0 | 0.0 | 0.6 | 24 | YMO-SSI |
| Saccharomycopsis schoenii | 10683 | 0.1 | 5.3 | 0.4 | 0.5 | 28.3 | 2.3 | 24 | YMO-SSI |
| Sacaharomycopsis synnaedendra | 1604 | 0.0 | 2.8 | 1.3 | 0.0 | 1.2 | 0.0 | 24 | YMO-SSI |
| Saccharomycopsis vini | 1748 | 0.0 | 3.9 | 0.4 | 0.0 | 23.2 | 6.4 | 24 | YMO-SSI |
| Saturnispora zaruensis | 1384 | 0.0 | 0.2 | 0.1 | 0.0 | 3.0 | 1.3 | 24 | YMO-SSI |
| Schizoblastosporion kobayasii | 1644 | 0.0 | 4.0 | 0.9 | 0.0 | 2.8 | 4.7 | 24 | YMO-SSI |
| Schizoblastosporion starkeyi-hennic | 10842 | 0.0 | 0.9 | 0.2 | 0.0 | 1.1 | 0.8 | 24 | YPDO-SSI |
| Sporopachydermia cereana | 10013 | 0.0 | 0.6 | 0.2 | 0.2 | 0.1 | 1.2 | 24 | YMO-SSI |
| Stephanoascus ciferii | 1854 | 0.0 | 0.9 | 0.1 | 0.0 | 3.3 | 0.0 | 24 | YMO-SSI |
| Sterigmatomyces elviae | 1843 | 0.0 | 4.5 | 0.5 | 0.1 | 10.5 | 1.8 | 24 | YMO-SSI |
| Sterigmatomyces halophilus | 1488 | 0.0 | 0.0 | 0.0 | 0.8 | 0.3 | 0.0 | 24 | YMO-SSI |
| Sterigmatosporidium polymorphum | 10121 | 0.0 | 2.4 | 0.1 | 0.0 | 15.7 | 1.3 | 24 | YMO-SSI |
| Sympodiomyces parvus | 10132 | 0.0 | 3.7 | 0.1 | 0.0 | 3.0 | 0.0 | 17 | YMO-SSI |
| Sympodiomycopsis paphiopedili | 10750 | 0.0 | 1.3 | 1.0 | 0.0 | 0.8 | 1.0 | 24 | YMO-SSI |
| Trichosporon brassicae | 1584 | 0.0 | 13.0 | 0.7 | 0.0 | 13.2 | 0.0 | 24 | YMO-SSI |
| Trichosporon pullulans | 1232 | 0.2 | 10.9 | 0.2 | 0.3 | 30.5 | 1.1 | 17 | YMO-SSI |
| Trigonopsis variabilis | 0755 | 0.0 | 0.0 | 0.0 | 0.0 | 0.1 | 0.2 | 24 | YMO-SSI |
| Tsuchiyaea wingfieldii | 10204 | 0.0 | 15.3 | 0.7 | 0.0 | 17.5 | 1.4 | 24 | YMO-SSI |
| Wickerhamilla domercqiae | 1857 | 0.0 | 1.7 | 0.0 | 0.0 | 5.2 | 0.0 | 24 | YMO-SSI |
| Xanthophyllomyces dendrorhous | 10130 | 0.1 | 30.0 | 0.8 | 0.5 | 33.8 | 2.8 | 24 | YMO-SSI |
| Zygozyma oligophaga | 10360 | 0.1 | 6.4 | 5.3 | 0.8 | 24.3 | 5.6 | 24 | YMO-SSI |

| | | Day 3 | | | Day 9 | | | Temp. | |
|---|---|---|---|---|---|---|---|---|---|
| Strains | No. | NOH | FOH | GGOH | NOH | FOH | GGOH | (° C.) | Medium |
| Aciculoconidium aculeatum | IFO 10124 | 0.0 | 21.3 | 1.4 | 0.0 | 26.4 | 2.3 | 24 | YMO-SSI |
| Bullera pseudoalba | IFO 10179 | 0.0 | 11.0 | 2.0 | 0.0 | 40.7 | 15.0 | 24 | YMO-SSI |
| Candida albicans | IFO 1060 | 0.2 | 108.8 | 3.5 | 0.8 | 32.9 | 4.7 | 30 | YMO-SSI |
| Candida glabrata | IFO 0741 | 0.3 | 19.6 | 0.6 | 3.2 | 70.1 | 4.2 | 30 | YMO-SSI |
| Candida guillermondii | IFO 0566 | 0.0 | 3.9 | 0.8 | 0.0 | 4.2 | 1.1 | 30 | YMO-SSI |
| Candida intermedia | IFO 0761 | 0.0 | 56.2 | 2.5 | 0.1 | 87.0 | 6.2 | 30 | YMo-SSI |
| Candida kefyr | IFO 0706 | 0.3 | 28.2 | 2.0 | 0.7 | 15.8 | 2.9 | 30 | YMO-SSI |
| Candida krusei | IFO 0941 | 0.5 | 37.9 | 4.0 | 3.7 | 7.8 | 8.0 | 30 | YMO-SSI |
| Candida tenuis | IFO 0716 | 0.0 | 2.2 | 0.7 | 0.0 | 31.2 | 2.2 | 30 | YMO-SSI |
| Candida utilis | IFO 0619 | 0.2 | 42.2 | 5.5 | 0.8 | 52.5 | 11.1 | 30 | YMO-SSI |
| Cryptococcus humicola | IFO 0753 | 0.2 | 6.3 | 2.0 | 0.0 | 0.3 | 3.3 | 30 | YMO-SSI |
| Cryptococcus terreus | IFO 0727 | 0.0 | 1.2 | 0.1 | 0.2 | 1.9 | 0.3 | 30 | YMO-SSI |
| Debaryomyces castellii | IFO 1359 | 0.0 | 11.4 | 1.1 | 0.0 | 26.8 | 4.6 | 30 | YMO-SSI |
| Fellomyces penicillatus | IFO 10119 | 0.0 | 2.9 | 0.3 | 0.1 | 45.7 | 4.4 | 24 | YMO-SSI |
| Filobasidium capsuligenum | IFO 1185 | 0.0 | 51.0 | 1.1 | 0.2 | 106.6 | 3.6 | 24 | YMO-SSI |
| Filobasidium uniguttulatum | IFO 0699 | 0.0 | 28.7 | 1.3 | 0.4 | 85.4 | 8.9 | 24 | YMO-SSI |
| Kloeckera corticis | IFO 0633 | 0.4 | 42.8 | 2.3 | 1.2 | 62.1 | 8.2 | 30 | YMO-SSI |
| Holtermannia corniformis | IFO 10742 | 0.0 | 25.4 | 2.8 | 1.1 | 50.7 | 8.4 | 24 | YMO-SSI |
| Kluyveromyces marxianus | IFO 0617 | 0.0 | 16.6 | 0.8 | 0.4 | 35.1 | 5.0 | 30 | YMO-SSI |
| Phaffia rhodozyma | ATCC 66270 | 0.0 | 2.2 | 0.1 | 0.5 | 108.7 | 5.8 | 24 | YMO-SSI |
| Pichia anomala | IFO 0146 | 0.2 | 34.8 | 2.6 | 0.2 | 7.4 | 4.3 | 30 | YMO-SSI |
| Pichia fabianii | IFO 1254 | 0.0 | 14.3 | 1.5 | 0.2 | 0.1 | 4.2 | 30 | YMO-SSI |
| Pichia farinosa | IFO 1003 | 0.0 | 3.2 | 0.6 | 0.0 | 11.1 | 1.8 | 30 | YMO-SSI |
| Pichia jadinii | IFO 0987 | 0.0 | 23.1 | 2.0 | 0.1 | 24.6 | 8.3 | 30 | YMO-SSI |
| Pichia polymorpha | IFO 0195 | 0.3 | 21.8 | 3.2 | 0.4 | 0.6 | 5.2 | 30 | YMO-SSI |
| Pichia silvicola | IFO 0807 | 0.2 | 10.6 | 1.6 | 0.8 | 29.0 | 4.2 | 30 | YMO-SSI |

TABLE 14-continued

| Production of nerolidol (NOH), farnesol (FOH) and geranylgeraniol (GGOH) (mg/L of culture solution) | | | | | | | | | |
|---|---|---|---|---|---|---|---|---|---|
| Rhodotorula glutinis | IFO 0695 | 0.0 | 3.8 | 0.2 | 0.0 | 3.4 | 0.3 | 30 | YMO-SSi |
| Rhodotorula minuta | IFO 0715 | 0.3 | 6.6 | 12.0 | 3.4 | 5.0 | 0.7 | 30 | YMO-SSi |
| Rhodotorula rubra | IFO 0870 | 0.3 | 5.5 | 10.8 | 3.5 | 4.4 | 26.4 | 30 | YMO-SSi |
| Saccharomyces cerevisiae | IFO 0258 | 0.0 | 22.3 | 0.6 | 0.4 | 77.5 | 1.9 | 30 | YMO-SSi |
| Saccharomyces cerevisiae | IFO 2347 | 0.0 | 18.8 | 0.7 | 0.1 | 36.5 | 1.4 | 30 | YMO-SSi |
| Saccharomycodes ludwigii | IFO 10036 | 0.0 | 3.3 | 0.2 | 0.1 | 15.5 | 0.4 | 24 | YMO-SSi |
| Saccharomycopsis fermentans | IFO 10772 | 0.1 | 41.4 | 1.9 | 0.3 | 37.9 | 3.1 | 24 | YMO-SSi |
| Sporidiobolus samonicolar | IFO 1035 | 0.1 | 7.9 | 1.1 | 0.1 | 42.3 | 6.4 | 30 | YMO-SSi |
| Sporobolomyces salmonicolar | IFO 0374 | 0.1 | 28.8 | 3.4 | 0.5 | 35.7 | 14.4 | 30 | YMO-SSi |
| Trichosporiella flavificans | IFO 1573 | 0.0 | 0.0 | 0.0 | 0.2 | 31.5 | 3.0 | 24 | YMO-SSi |
| Trichosporon penicillatum | IFO 2171 | 0.0 | 1.7 | 0.6 | 0.1 | 1.7 | 0.0 | 30 | YMO-SSi |
| Williopsis californica | IFO 0800 | 10.1 | 95.7 | 4.7 | 10.5 | 90.1 | 5.2 | 24 | YMO-SSi |
| Willopsis saturnus | IFO 0895 | 0.5 | 59.1 | 9.0 | 1.6 | 69.2 | 13.1 | 30 | YMO-SSi |
| Yamadazyma farinosa | IFO 0459 | 0.0 | 6.2 | 0.8 | 0.0 | 20.8 | 2.2 | 30 | YMO-SSi |
| Zygoascus hellenicus | IFO 10184 | 0.0 | 3.9 | 0.1 | 0.0 | 32.4 | 2.7 | 24 | YMO-SSi |

What is claimed is:

1. A method for producing geranylgeraniol and/or farnesol, which comprises culturing geranylgeraniol- and/or farnesol-producing cells belonging to any one of the following genera:

Saccharomyces,
Saccharomycopsis,
Saccharomycodes,
Schizosaccharomyces,
Wickerhamia,
Debaryomyces,
Hanseniaspora,
Pichia,
Kloeckera,
Candida,
Zygosaccharomyces,
Ogataea,
Williopsis,
Kluyveromyces,
Cryptococcus,
Bacillus,
Staphylococcus,
Pseudomonas,
Ambrosiozyma,
Metschnikowia,
Trichosporon,
Bullera,
Filobasidium,
Rhodotorula, and
Brevibacterium, or any one of the following species
Hansenula polymorpha,
Lypomyces starkeyi,
Kuraishia capsulata,
Komagataella pastoris,
Yarrowia lipolytica,
Nakazawaea holstii,
Torulaspora delbrueckii,
Citeromyces matritensis,
Waltomyces lipofer,
Micrococcus luteus,
Exiguobacterium acetylicum,
Mucor javanicus,
Cystofilobasidium infirmominiatum,
Xanthophyllomyces dendrorhons,
Fellomyces penicillatus,
Holtermannia corniformis,
Phaffia rhodozyma,
Sporidiobolus samonicolar,
Sporobolomyces salmonicolor,
Zygoascus hellenicus,
Haloferax volcanii,
Leucosporidium scottii,
Myxozyma lipomycoides,
Trichosporiella flavificans, and
Alcaligenes faecalis, in a medium with a sugar content of 1–10% in the presence of at least one member selected from the group consisting of a soybean oil, fish oil, almond oil and olive oil at a concentration of about 0.1% or more to produce and accumulate geranylgeraniol and/or farnesol in the cells and/or in the extracellular environment; and then collecting geranylgeraniol and/or farnesol.

2. The method of claim 1 wherein the medium has a sugar content of 2–7%.

* * * * *

UNITED STATES PATENT AND TRADEMARK OFFICE
CERTIFICATE OF CORRECTION

PATENT NO. : 6,972,191 B2
APPLICATION NO. : 10/022695
DATED : December 6, 2005
INVENTOR(S) : Muramatsu et al.

It is certified that error appears in the above-identified patent and that said Letters Patent is hereby corrected as shown below:

| Column | Line | |
|---|---|---|
| 3 | 50 | Change "Saccaromycodies ludwiggi" to --Saccharomycodes ludwigii--. |
| 3 | 63 | Change "erogosterol" to --ergosterol--. |
| 4 | 9 | Change "(SQAD." to --(SQAD)--. |
| 4 | 57 | Change "Schizosaccharornyces" to --Schizosaccharomyces-- |
| 7 | 65 | Change "samonicolar" to --salmonicolor--. |
| 9 | 39 | Change "Toxiocology" to --Toxicology--. |
| 15 | 56 | Change "saturuns" to --saturnus--. |
| 10 | 51 | Change "Tesler coil" to --Tesla coil--. |
| 27 | 36 | Change "Rhodotorula aurantinaca" to --Rhodotorula aurantiaca--. |

UNITED STATES PATENT AND TRADEMARK OFFICE
CERTIFICATE OF CORRECTION

PATENT NO. : 6,972,191 B2
APPLICATION NO. : 10/022695
DATED : December 6, 2005
INVENTOR(S) : Muramatsu et al.

It is certified that error appears in the above-identified patent and that said Letters Patent is hereby corrected as shown below:

| Column | Line | |
|---|---|---|
| 27 | 44 | Change "Yerroiwa" to --Yarrowia--. |
| 29 | 30 | Change "starkeyi-hennic" to --starkeyi-henricii--. |
| 31 | 11 | Change "Sporidiobolus samonicolar" to --Sporidiobolus salmonicolor--. |
| 31 | 12 | Change "Sporobolomyces salmonicolar" to --Sporobolomyces salmonicolor--. |
| 32 | | Change "Sporidiobolus samonicolar" to --Sporidiobolus salmonicolor--. |

Signed and Sealed this

Twenty-sixth Day of September, 2006

JON W. DUDAS
*Director of the United States Patent and Trademark Office*